(12) United States Patent
Barrow et al.

(10) Patent No.: US 6,235,759 B1
(45) Date of Patent: May 22, 2001

(54) DIHYDROPYRIDINONES AND PYRROLINONES USEFUL AS ALPHA 1A ADRENOCEPTOR ANTAGONISTS

(75) Inventors: James C. Barrow, Harleysville; Philippe G. Nanterment, Lansdale; Harold G. Selnick, Ambler, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/428,973

(22) Filed: Oct. 28, 1999

Related U.S. Application Data

(60) Provisional application No. 60/141,463, filed on Jun. 29, 1999, and provisional application No. 60/106,095, filed on Oct. 29, 1998.

(51) Int. Cl.[7] .................. A61K 31/44; C07D 213/62
(52) U.S. Cl. .................. 514/335; 514/345; 546/261; 546/290
(58) Field of Search .................. 514/335, 345; 546/261, 290

(56) References Cited

U.S. PATENT DOCUMENTS

| | | |
|---|---|---|
| 4,661,491 | 4/1987 | Regnier . |
| 5,620,993 | 4/1997 | Patane et al. . |
| 5,767,131 | 6/1998 | Gluchowski et al. . |
| 5,942,517 * | 8/1999 | Nagarathnam et al. ............ 514/274 |

FOREIGN PATENT DOCUMENTS

| | | |
|---|---|---|
| WO92/00073 | 9/1992 | (WO) . |
| WO92/16213 | 10/1992 | (WO) . |
| WO94/08040 | 4/1994 | (WO) . |
| WO94/22829 | 10/1994 | (WO) . |
| WO96/14846 | 5/1996 | (WO) . |
| WO96/40135 | 12/1996 | (WO) . |
| WO97/17969 | 5/1997 | (WO) . |
| WO97/42956 | 11/1997 | (WO) . |

OTHER PUBLICATIONS

Hartman et al. "Coexpression of two distinct muscle acetyl choline . . . " CA 114:182447, 1990.*
Martin–Moutot et al. "Properties of omega conotoxin MVIIC receptors . . . " CA 123:76811, 1995.*
Morales et al., J. Heterocycl. Chem., 1996, 33, 103–107.
Verdecia et al., J. Chem. Soc., Perkin Trans., 1996, 1, 947–951.
Svetlik et al., J. Chem. Soc., Perkin Trans., 1990, 1, 1315–1318.
Peseke, et al., "Prodecure for the preparation of furfuryl–substituted tetrahydronicotinonitriles", 1987, Chemical Abstracts No. 109: 149358 on STN (Abstract of Patent No. DD250122).
Gluchowski et al., "Dihydropyridine derivatives for treatment of benign prostatic hyperplasia", 1994, Chemical Abstracts No. 129: 67709 on STN (Abstract of WO 9422829).

* cited by examiner

Primary Examiner—Celia Chang
(74) Attorney, Agent, or Firm—Catherine D. Fitch; Kenneth R. Walton; Melvin Winokur

(57) ABSTRACT

Novel dihydropyridinone and pyrrolinone compounds and pharmaceutically acceptable salts thereof are disclosed. The synthesis of these compounds and their use as alpha 1*a* adrenergic receptor antagonists is also described. One application of these compounds is in the treatment of benign prostatic hyperplasia. These compounds are selective in their ability to relax smooth muscle tissue enriched in the alpha 1*a* receptor subtype without at the same time inducing hypotension. One such tissue is found surrounding the urethral lining. Therefore, one utility of the instant compounds is to provide acute relief to males suffering from benign prostatic hyperplasia, by permitting less hindered urine flow. Another utility of the instant compounds is provided by combination with a human 5-alpha reductase inhibitory compound, such that both acute and chronic relief from the effects of benign prostatic hyperplasia can be achieved.

28 Claims, No Drawings

DIHYDROPYRIDINONES AND PYRROLINONES USEFUL AS ALPHA 1A ADRENOCEPTOR ANTAGONISTS

This application claims the benefit of U.S. Provisional Application No. 60/106,095, filed Oct. 29, 1998 and U.S. Provisional Application No. 60/141,463, filed Jun. 29, 1999.

FIELD OF THE INVENTION

This invention relates to certain dihydropyridinone and pyrrolinone compounds and pharmaceutically acceptable salts thereof, their synthesis, and their use as alpha 1a adrenoceptor antagonists. More particularly, the compounds of the present invention are useful for treating benign prostatic hyperplasia (BPH).

References are made throughout this application to various publications, the disclosures of which are hereby incorporated by reference in their entireties in order to more fully describe the state of the art to which this invention pertains.

BACKGROUND OF THE INVENTION

Human adrenergic receptors are integral membrane proteins which have been classified into two broad classes, the alpha and the beta adrenergic receptors. Both types mediate the action of the peripheral sympathetic nervous system upon binding of catecholamines, norepinephrine and epinephrine.

Norepinephrine is produced by adrenergic nerve endings, while epinephrine is produced by the adrenal medulla. The binding affinity of adrenergic receptors for these compounds forms one basis of the classification: alpha receptors bind norepinephrine more strongly than epinephrine and much more strongly than the synthetic compound isoproterenol. The binding affinity of these hormones is reversed for the beta receptors. In many tissues, the functional responses, such as smooth muscle contraction, induced by alpha receptor activation are opposed to responses induced by beta receptor binding.

Subsequently, the functional distinction between alpha and beta receptors was further highlighted and refined by the pharmacological characterization of these receptors from various animal and tissue sources. As a result, alpha and beta adrenergic receptors were further subdivided into alpha 1, alpha 2, $\beta_1$, and $\beta_2$ subtypes. Functional differences between alpha 1 and alpha 2 receptors have been recognized, and compounds which exhibit selective binding between these two subtypes have been developed.

For a general background on the alpha adrenergic receptors, the reader's attention is directed to Robert R. Ruffolo, Jr., *a-Adrenoreceptors: Molecular Biology, Biochemistry and Pharmacology*, (*Progress in Basic and Clinical Pharmacology* series, Karger, 1991), wherein the basis of alpha 1/alpha 2 subclassification, the molecular biology, signal transduction (G-protein interaction and location of the significant site for this and ligand binding activity away from the 3'-terminus of alpha adrenergic receptors), agonist structure-activity relationships, receptor functions, and therapeutic applications for compounds exhibiting alpha-adrenergic receptor affinity was explored.

The cloning, sequencing and expression of alpha receptor subtypes from animal tissues has led to the subclassification of the alpha 1 receptors into alpha 1d (formerly known as alpha 1a or 1a/1d), alpha 1b and alpha 1a (formerly known as alpha 1c) subtypes. Each alpha 1 receptor subtype exhibits its own pharmacologic and tissue specificities. The designation "alpha 1a" is the appellation recently approved by the IUPHAR Nomenclature Committee for the previously designated "alpha 1c" cloned subtype as outlined in the 1995 Receptor and Ion Channel Nomenclature Supplement (Watson and Girdlestone, 1995). The designation alpha 1a is used throughout this application to refer to this subtype. At the same time, the receptor formerly designated alpha 1a was renamed alpha 1d. The new nomenclature is used throughout this application. Stable cell lines expressing these alpha 1 receptor subtypes are referred to herein; however, these cell lines were deposited with the American Type Culture Collection (ATCC) under the old nomenclature. For a review of the classification of alpha 1 adrenoceptor subtypes, see, Martin C. Michel, et al., *Naunyn-Schmiedeberg's Arch. Pharmacol.* (1995) 352:1–10.

The differences in the alpha adrenergic receptor subtypes have relevance in pathophysiologic conditions. Benign prostatic hyperplasia, also known as benign prostatic hypertrophy or BPH, is an illness typically affecting men over fifty years of age, increasing in severity with increasing age. The symptoms of the condition include, but are not limited to, increased difficulty in urination and sexual dysfunction. These symptoms are induced by enlargement, or hyperplasia, of the prostate gland. As the prostate increases in size, it impinges on free-flow of fluids through the male urethra. Concomitantly, the increased noradrenergic innervation of the enlarged prostate leads to an increased adrenergic tone of the bladder neck and urethra, further restricting the flow of urine through the urethra.

In benign prostatic hyperplasia, the male hormone 5alpha-dihydrotestosterone has been identified as the principal culprit. The continual production of 5a-dihydrotestosterone by the male testes induces incremental growth of the prostate gland throughout the life of the male. Beyond the age of about fifty years, in many men, this enlarged gland begins to obstruct the urethra with the pathologic symptoms noted above.

The elucidation of the mechanism summarized above has resulted in the recent development of effective agents to control, and in many cases reverse, the pernicious advance of BPH. In the forefront of these agents is Merck & Co., Inc.'s product PROSCAR® (finasteride). The effect of this compound is to inhibit the enzyme testosterone 5-a reductase, which converts testosterone into 5a-dihydrotesterone, resulting in a reduced rate of prostatic enlargement, and often reduction in prostatic mass.

The development of such agents as PROSCAR® bodes well for the long-term control of BPH. However, as may be appreciated from the lengthy development of the syndrome, its reversal also is not immediate. In the interim, those males suffering with BPH continue to suffer, and may in fact lose hope that the agents are working sufficiently rapidly.

In response to this problem, one solution is to identify pharmaceutically active compounds which complement slower-acting therapeutics by providing acute relief. Agents which induce relaxation of the lower urinary tract tissue, by binding to alpha 1 adrenergic receptors, thus reducing the increased adrenergic tone due to the disease, would be good candidates for this activity. Thus, one such agent is alfuzosin, which is reported in EP 0 204597 to induce urination in cases of prostatic hyperplasia. Likewise, in WO 92/00073, the selective ability of the R(+) enantiomer of terazosin to bind to adrenergic receptors of the alpha 1 subtype was reported. In addition, in WO 92/16213, combinations of 5a-reductase inhibitory compounds and alpha1-adrenergic receptor blockers (terazosin, doxazosin, prazosin, bunazosin, indoramin, alfuzosin) were disclosed. However, no information as to the alpha 1d, alpha 1b, or alpha 1a subtype specificity of these compounds was provided as this data and its relevancy to the treatment of BPH was not known. Current therapy for BPH uses existing non-selective alpha 1 antagonists such as prazosin (Minipress, Pfizer), Terazosin (Hytrin, Abbott) or doxazosin mesylate (Cardura, Pfizer). These non-selective antagonists suffer from side effects related to antagonism of the alpha 1d and alpha 1b receptors in the peripheral vasculature, e.g., hypotension and syncope.

The relatively recent cloning of the human alpha 1a adrenergic receptor (ATCC CRL 11140) and the use of a screening assay utilizing the cloned human alpha 1a receptor has enabled identification of compounds which specifically interact with the human alpha 1a adrenergic receptor. For further description, see WO 94/08040 and WO 94/10989. As disclosed in the instant patent disclosure, a cloned human alpha 1a adrenergic receptor and a method for identifying compounds which bind the human alpha 1a receptor has made possible the identification of selective human alpha 1a adrenergic receptor antagonists useful for treating BPH.

Several classes of compounds have been disclosed to be selective alpha 1a adrenergic receptor antagonists useful for treating BPH. WO 94/22829 discloses, for example, certain 4-(un)substituted phenyl-1,4-dihydropyridine derivatives which are described as potent, selective alpha 1a antagonists with weak calcium channel antagonistic activity and which are further described to be anticipated as useful for treating BPH. WO 94/22829 also discloses (see pages 30–35) a broad collection of oxo-substituted, 6-membered hetero-cycle and carbocycle derivatives which generally embraces certain dihydropyridinones. As another example, WO 96/14846, WO 97/17969 and WO 97/42956 each disclose certain dihydropyrimidine derivatives (e.g., certain 1,2,3,6-tetrahydro-2-oxo-pyrimidine derivatives) which are selective antagonists for the human alpha 1a receptor and useful for treatment of BPH, impotency, cardiac arrhythmia, and other diseases where antagonism of the alpha 1a receptor may be useful. As still another example, WO 96/40135 discloses, inter alia, certain phenylpiperidinyl alkyl saccharin derivatives and their use as selective alpha 1a antagonists.

The instant patent disclosure discloses novel dihydropyridinone and pyrrolinone compounds which selectively bind to the human alpha 1a receptor. These compounds are further tested for binding to other human alpha 1 receptor subtypes, as well as counterscreened against other types of receptors (e.g., alpha 2), thus defining the specificity of the compounds of the present invention for the human alpha 1a adrenergic receptor.

It is an object of the present invention to identify compounds which bind to the alpha 1a adrenergic receptor. It is a further object of the invention to identify compounds which act as antagonists of the alpha 1a adrenergic receptor. It is another object of the invention to identify alpha 1a adrenergic receptor antagonist compounds which are useful agents for treating BPH in animals, preferably mammals, especially humans. Still another object of the invention is to identify alpha 1a adrenergic receptor antagonists which are useful for relaxing lower urinary tract tissue in animals, preferably mammals, especially humans.

The compounds of the present invention are alpha 1a adrenergic receptor antagonists. Thus, the compounds of the present invention are useful for treating BPH in mammals. Additionally, it has been found that the alpha 1a adrenergic receptor antagonists of the present invention are also useful for relaxing lower urinary tract tissue in mammals.

SUMMARY OF THE INVENTION

The present invention provides dihydropyridinone and pyrrolinone compounds for the treatment of urinary obstruction caused by benign prostatic hyperplasia (BPH). The compounds antagonize the human alpha 1a adrenergic receptor at nanomolar and subnanomolar concentrations while typically exhibiting at least about ten fold lower affinity for the alpha 1d and alpha 1b human adrenergic receptors and many other G-protein coupled receptors. This invention has the advantage over non-selective alpha 1 adrenoceptor antagonists of reduced side effects related to peripheral adrenergic blockade. Such side effects include hypotension, syncope, lethargy, etc.

More particularly, the present invention is a compound of formula (I):

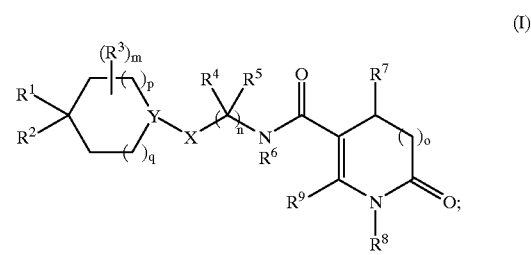

wherein
Y is CH or N;
X is $CR^4R^5$, when Y is N;
X is $NR^6$, when Y is CH;
$R^1$ is phenyl, mono- or poly-substituted phenyl, naphthyl, mono- or poly-substituted naphthyl, heterocyclic, or mono- or poly-substituted heterocyclic; wherein the heterocyclic is selected from the group consisting of pyridyl, pyrazinyl, thienyl, thiazolyl, furanyl and quinazolinyl; each of the substituents on the substituted phenyl or substituted naphthyl is independently selected from halo, nitro, cyano, hydroxy, $C_1$–$C_6$ alkyl, $C_3$–$C_8$ cycloalkyl, $C_1$–$C_6$ alkoxy, halogenated $C_1$–$C_6$ alkyl, halogenated $C_3$–$C_8$ cycloalkyl, halogenated $C_1$–$C_6$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substitutents on the substituted heterocyclic is independently selected from halo, cyano, nitro, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $C_3$–$C_8$ cycloalkyl, and halogenated $C_3$–$C_8$ cycloalkyl;
$R^2$ is hydrogen, cyano, hydroxy, $C_1$–$C_6$ alkoxy, $CO_2R^c$, $C(=O)N(R^c)_2$, tetrazole, isooxadiazole, phenyl, mono- or poly-substituted phenyl, naphthyl, mono- or poly-substituted naphthyl, heterocyclic, or mono- or poly-substituted heterocyclic; wherein the heterocyclic is selected from the group consisting of pyridyl, thienyl and furanyl; each of the substituents on the substituted phenyl or substituted naphthyl is independently selected from halo, cyano, nitro, hydroxy, $C_1$–$C_6$ alkoxy, halogenated $C_1$–$C_6$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, $(CH_2)_{0-4}SO_2R^c$, $C_1–C_6$ alkyl, halogenated $C_1–C_6$ alkyl, $C_3–C_8$ cycloalkyl, and halogenated $C_3–C_8$ cycloalkyl; and each of the substituents on the substituted heterocyclic is independently selected from halo, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl $C_1–C_6$alkyl, halogenated $C_1–C_6$ alkyl, $C_1–C_6$ alkoxy, halogenated $C_1–C_6$ alkoxy, $(CH_2)_{1-4}OR^a$, $C_3–C_8$ cycloalkyl, and halogenated $C_3–C_8$ cycloalkyl; each $R^3$ is a substituent connected to a ring atom other than $CR^1R^2$ or Y and is independently $C_1–C_4$ alkyl;

$R^4$ and $R^5$ are each independently selected from hydrogen, $C_1–C_6$ alkyl, and $C_3–C_8$ cycloalkyl;

$R^6$ is hydrogen or $C_1–C_4$ alkyl;

$R^7$ is phenyl, or mono- or poly-substituted phenyl; wherein each of the substituents on the substituted phenyl is independently selected from halo, nitro, cyano, hydroxy, $C_1–C_6$ alkyl, $C_3–C_8$ cycloalkyl, $C_1–C_6$ alkoxy, halogenated $C_1–C_6$ alkyl, halogenated $C_3–C_8$ cycloalkyl, halogenated $C_1–C_6$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$;

$R^8$ is hydrogen, $C_1–C_6$ alkyl, $(CH_2)_{0-4}CO_2R^c$, or $(CH_2)_{0-4}C(=O)R^c$;

$R^9$ is hydrogen, halo, cyano, $C_1–C_6$ alkyl, $C_3–C_8$ cycloalkyl, $C_1–C_6$ alkoxy, halogenated $C_1–C_6$ alkyl, halogenated $C_3–C_8$ cycloalkyl, halogenated $C_1–C_6$ alkoxy, $(CH_2)_{1-4}OR^b$, $CO_2R^c$, $C(=O)R^c$, or $C(=O)N(R^c)_2$;

$R^a$ is hydrogen, $C_1–C_6$ alkyl, or halogenated $C_1–C_6$ alkyl;

$R^b$ is hydrogen, $C_1–C_6$ alkyl, or halogenated $C_1–C_6$ alkyl;

$R^c$ and $R^d$ are each independently selected from hydrogen, $C_1–C_6$ alkyl, $C_3–C_8$ cycloalkyl and $(CH_2)_{1-4}CF_3$;

m is an integer of from 0 to 2;

n is an integer of from 1 to 4, when X is $NR^6$;

n is an integer of from 0 to 3, when X is $CR^4R^5$;

o is an integer equal to 0 or 1; and p and q are each integers of from 0 to 2, wherein the sum of p+q is less than or equal to 3;

or a pharmaceutically acceptable salt thereof.

The present invention also includes pharmaceutical compositions, methods of preparing pharmaceutical compositions, and methods of treatment.

These and other embodiments, aspects and features of the present invention are either further described in or will be apparent from the ensuing description, examples and appended claims.

DETAILED DESCRIPTION OF THE INVENTION

The present invention includes dihydropyridinone and pyrrolinone compounds of Formula (I) above. These compounds and their pharmaceutically acceptable salts are useful as selective alpha 1a antagonists.

In a first embodiment, the present invention is a compound of Formula (I), wherein $R^1$ is phenyl, mono- or di-substituted phenyl, naphthyl, mono- or di-substituted naphthyl, heterocyclic, or mono- or di-substituted heterocyclic;

$R^2$ is hydrogen, cyano, hydroxy, $C_1–C_6$ alkoxy, $CO_2R^c$, $C(=O)N(R^c)_2$, tetrazole, isooxadiazole, phenyl, mono- or di-substituted phenyl, naphthyl, mono- or di-substituted naphthyl, heterocyclic, or mono- or di-substituted heterocyclic;

$R^7$ is selected from phenyl, or mono- or di-substituted phenyl;

and all other variables are as originally defined above;

or a pharmaceutically acceptable salt thereof.

In a second embodiment, the present invention is a compound of Formula (I), wherein $R^1$ is phenyl, mono- or di-substituted phenyl, pyridyl, or mono-or di-substituted pyridyl; wherein each of the substituents on the substituted phenyl is independently selected from halo, cyano, hydroxy, $C_1–C_4$ alkyl, $C_1–C_4$ alkoxy, halogenated $C_1–C_4$ alkyl, halogenated $C_1–C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substituents on the substituted pyridyl is independently selected from halo, cyano, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1–C_4$ alkyl, halogenated $C_1–C_4$ alkyl, $C_1–C_4$ alkoxy, halogenated $C_1–C_4$ alkoxy, and $(CH_2)_{1-4}OR^a$;

$R^2$ is hydrogen, cyano, hydroxy, $C_1–C_4$ alkoxy, $CO_2R^c$, $C(=O)N(R^c)_2$, phenyl, mono- or di-substituted phenyl, pyridyl, or mono- or di-substituted pyridyl; wherein each of the substituents on the substituted phenyl is independently selected from halo, cyano, hydroxy, $C_1–C_4$ alkyl, $C_1–C_4$ alkoxy, halogenated $C_1–C_4$ alkyl, halogenated $C_1–C_4$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, and $(CH_2)_{0-4}SO_2R^c$; and each of the substituents on the substituted pyridyl is independently selected from halo, $C_1–C_4$ alkyl, halogenated $C_1–C_4$ alkyl, $C_1–C_4$ alkoxy, halogenated $C_1–C_4$ alkoxy, $(CH_2)_{1-4}OR^a$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$;

$R^7$ is phenyl, or mono- or poly-substituted phenyl; wherein each of the substituents on the substituted phenyl is independently selected from halo, cyano, hydroxy, $C_1–C_4$ alkyl, $C_1–C_4$ alkoxy, halogenated $C_1–C_4$ alkyl, halogenated $C_1–C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, and $SO_2R^c$;

$R^a$ is hydrogen, $C_1–C_4$ alkyl, or halogenated $C_1–C_4$ alkyl;

$R^b$ is hydrogen, $C_1–C_4$ alkyl, or halogenated $C_1–C_4$ alkyl;

$R^c$ and $R^d$ are each independently selected from hydrogen, $C_1–C_4$ alkyl and $(CH_2)_{1-2}CF_3$;

and all other variables are as originally defined above;

or a pharmaceutically acceptable salt thereof.

In a third embodiment, the present invention is a compound of Formula (I), wherein $R^1$ is phenyl, or mono- or di-substituted phenyl, pyridyl, or mono- or di-substituted pyridyl; wherein each of the substituents on the substituted phenyl is independently selected from halo, cyano, hydroxy, $C_1–C_4$ alkyl, $C_1–C_4$ alkoxy, halogenated $C_1–C_4$ alkyl, halogenated $C_1–C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substituents on the substituted pyridyl is independently selected from halo, cyano, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1–C_4$ alkyl, halogenated $C_1–C_4$ alkyl, $C_1–C_4$ alkoxy, halogenated $C_1–C_4$ alkoxy, and $(CH_2)_{1-4}OR^a$;

$R^2$ is hydrogen, cyano, hydroxy, $C_1$–$C_6$ alkoxy, $CO_2R^c$, or $C(=O)N(R^c)_2$;

$R^4$ and $R^5$ are either both hydrogen, or one of $R^4$ and $R^5$ is hydrogen and the other is hydrogen, $C_1$–$C_6$ alkyl, or $C_3$–$C_8$ cycloalkyl;

$R^7$ is phenyl, or mono- or di-substituted phenyl; wherein each of the substituents on the substituted phenyl is independently selected from halo, cyano, hydroxy, $C_1$–$C_4$ alkyl, $C_1$–$C_4$ alkoxy, $(CH_2)_{1-4}OR^b$, $(CH_2)_{0-4}CF_3$, $OCF_3$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, and $SO_2R^c$;

$R^b$ is $C_1$–$C_4$ alkyl or $CF_3$;

and all other variables are as originally defined above;

or a pharmaceutically acceptable salt thereof.

Other embodiments of the present invention include a compound of Formula (I), wherein n is an integer of from 2 to 4, when X is $NR^6$;

n is an integer of from 1 to 3, when X is $CR^4R^5$;

o is an integer equal to 0 or 1, provided that when Y is N, o is zero; and all other variables are as originally defined above, or as defined above in any one of the first, second, and third embodiments;

or a pharmaceutically acceptable salt thereof.

In a first class of the invention is a compound of Formula (II):

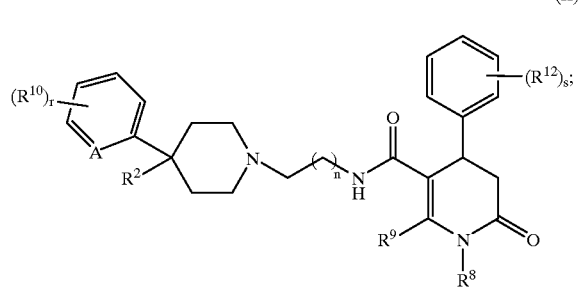

(II)

wherein

A is $CR^{10}$ or N;

$R^2$ is hydrogen, cyano, hydroxy, $C_1$–$C_6$ alkoxy, $CO_2R^c$, $C(=O)N(R^c)_2$, phenyl, or mono- or poly-substituted phenyl; wherein each of the substituents on the substituted phenyl is independently selected from halo, cyano, nitro, hydroxy, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, and $(CH_2)_{0-4}SO_2R^c$;

$R^8$ is hydrogen, $C_1$–$C_4$ alkyl, $(CH_2)_{0-4}CO_2R^c$, or $(CH_2)_{0-4}C(=O)R^c$;

$R^9$ is hydrogen, halo, cyano, $C_1$–$C_6$ alkyl, $C_3$–$C_6$ cycloalkyl, $C_1$–$C_6$ alkoxy, halogenated $C_1$–$C_6$ alkyl, halogenated $C_1$–$C_6$ alkoxy, $(CH_2)_{1-4}OR^b$, $CO_2R^c$, $C(=O)R^c$, or $C(=O)N(R^c)_2$;

$R^{10}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

$R^{12}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

$R^a$ is hydrogen, $C_1$–$C_6$ alkyl, or halogenated $C_1$–$C_6$ alkyl;

$R^b$ is hydrogen, $C_1$–$C_6$ alkyl, or halogenated $C_1$–$C_6$ alkyl;

$R^c$ and $R^d$ are each independently selected from hydrogen, $C_1$–$C_6$ alkyl, $C_3$–$C_8$ cycloalkyl and $(CH_2)_{1-4}CF_3$;

n is an integer of from 0 to 3; and r and s are independently integers of from 0 to 2;

or a pharmaceutically acceptable salt thereof.

In one aspect, the compound of Formula (II) is a (+) enantiomer or a pharmaceutically acceptable salt thereof. In another aspect, the compound of Formula (II) is a (−) enantiomer or a pharmaceutically acceptable salt thereof.

In a sub-class of the first class is a compound of Formula (II), wherein $R^2$ is hydrogen, cyano, hydroxy, $C_1$–$C_4$ alkoxy, $CO_2R^c$, $C(=O)N(R^c)_2$, phenyl, or mono- or poly-substituted phenyl; wherein each of the substituents on the substituted phenyl is independently selected from halo, cyano, hydroxy, $C_1$–$C_4$ alkyl, halogenated $C_1$–$C_4$ alkyl, $C_1$–$C_4$ alkoxy, halogenated $C_1$–$C_4$ alkoxy, $CO_2R^c$, $C(=O)N(R^c)_2$, $N(R^c)_2$, $NR^cC(=O)R^d$, $NR^cC(=O)N(R^d)_2$, $NR^cSO_2R^d$, $SO_2N(R^c)_2$, and $SO_2R^c$;

$R^8$ is hydrogen, $C_1$–$C_4$ alkyl, $CO_2R^c$, or $C(=O)R^c$;

$R^9$ is hydrogen, halo, cyano, $C_1$–$C_4$ alkyl, $C_3$–$C_6$ cycloalkyl, $C_1$–$C_4$ alkoxy, halogenated $C_1$–$C_4$ alkyl, halogenated $C_1$–$C_4$ alkoxy, $(CH_2)_{1-4}OR^b$, $CO_2R^c$, $C(=O)R^c$, or $C(=O)N(R^c)_2$;

$R^{10}$ is hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

$R^{12}$ is hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

$R^a$ is hydrogen, $C_1$–$C_4$ alkyl, or halogenated $C_1$–$C_4$ alkyl;

$R^b$ is hydrogen, $C_1$–$C_4$ alkyl, or halogenated $C_1$–$C_4$ alkyl;

$R^c$ and $R^d$ are each independently selected from hydrogen and $C_1$–$C_4$ alkyl;

n is an integer of from 1 to 3;

and all other variables are as originally defined above for the first class;

or a pharmaceutically acceptable salt thereof.

In an aspect of the preceding sub-class, $R^2$ is hydrogen, cyano, hydroxy, $C_1$–$C_4$ alkoxy, $CO_2R^c$, or $C(=O)N(R^c)_2$;

and all other variables are as defined in the sub-class;

or a pharmaceutically acceptable salt thereof.

In another sub-class of the first class is a compound of Formula (IIa):

(IIa)

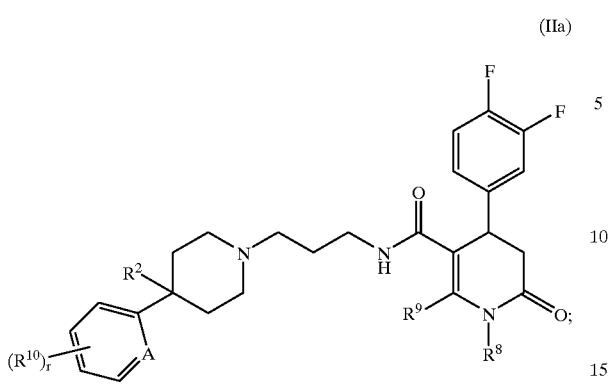

wherein
A is $CR^{10}$ or N;
$R^2$ is hydrogen, cyano, hydroxy, $C_1$–$C_6$ alkoxy, $CO_2R^c$, $C(=O)N(R^c)_2$, phenyl, or mono- or poly-substituted phenyl; wherein each of the substituents on the substituted phenyl is independently selected from fluoro, cyano, hydroxy, $C_1$–$C_4$ alkyl, $(CH_2)_{0-3}CF_3$, $OCF_3$, and $(CH_2)_{1-3}OCF_3$;
$R^8$ is hydrogen or $C_1$–$C_4$ alkyl;
$R^9$ is hydrogen, $C_1$–$C_4$ alkyl, $C_1$–$C_4$ alkoxy, $(CH_2)_{0-3}CF_3$, $OCF_3$, $(CH_2)_{1-3}OCF_3$, $CO_2R^c$, $C(=O)R^c$, or $C(=O)N(R^c)_2$;
each $R^{10}$ is independently hydrogen, fluoro, cyano, hydroxy, $C_1$–$C_4$ alkyl, $(CH_2)_{0-3}CF_3$, $OCF_3$, or $(CH_2)_{1-3}OCF_3$;
each $R^c$ is independently hydrogen, $C_1$–$C_4$ alkyl, or $(CH_2)_{1-4}CF_3$; and
r is an integer of from 0 to 2;
or a pharmaceutically acceptable salt thereof.

In one aspect, the compound of Formula (IIa) is a (+) enantiomer or a pharmaceutically acceptable salt thereof. In another aspect, the compound of Formula (IIa) is a (−) enantiomer or a pharmaceutically acceptable salt thereof.

Exemplifying the invention is a compound selected from the group consisting of:
4-(R)-(3,4-difluorophenyl)-6-methyl-3,4-dihydro-2-pyridinone-5-carboxylic acid{3-[4-(2-pyridyl)-piperidine-1-yl]-propyl}amide;
4-(R)-(3,4-difluorophenyl)-1,6-dimethyl-3,4-dihydro-2-pyridinone-5-carboxylic acid{3-[4-(2-pyridyl)-piperidine-1-yl]-propyl}amide;
4-(R)-(3,4-difluorophenyl)-6-methyl-3,4-dihydro-2-pyridinone-5-carboxylic acid{3-[4-(2-pyridyl)-4-cyano-piperidine-1-yl]-propyl}amide;
4-(R)-(3,4-difluorophenyl)-1,6-dimethyl-3,4-dihydro-2-pyridinone-5-carboxylic acid{3-[4-(2-pyridyl)-4-cyano-piperidine-1-yl]-propyl}amide;
4-(R)-(3,4-difluorophenyl)-6-methyl-3,4-dihydro-2-pyridinone-5-carboxylic acid{3-[4-(4-fluorophenyl)-piperidine-1-yl]-propyl}amide;
4-(S)-(3,4-difluorophenyl)-6-methyl-3,4-dihydro-2-pyridinone-5-carboxylic acid{3-[4-(4-fluorophenyl)-piperidine-1-yl]-propyl}amide;
4-(R)-(3,4-difluorophenyl)-1,6-dimethyl-3,4-dihydro-2-pyridinone-5-carboxylic acid{3-[4-(4-fluorophenyl)-piperidine-1-yl]-propyl}amide;
4-(S)-(3,4-difluorophenyl)-1,6-dimethyl-3,4-dihydro-2-pyridinone-5-carboxylic acid{3-[4-(4-fluorophenyl)-piperidine-1-yl]-propyl}amide;
4-(R)-(3,4-difluorophenyl)-6-methyl-3,4-dihydro-2-pyridinone-5-carboxylic acid{3-[4-(2-cyano-4-fluorophenyl)-piperidine-1-yl]-propyl}amide;
4-(R)-(3,4-difluorophenyl)-1,6-dimethyl-3,4-dihydro-2-pyridinone-5-carboxylic acid{3-[4-(2-cyano-4-fluorophenyl)-piperidine-1-yl]-propyl}amide;
4-(R)-(3,4-difluorophenyl)-6-methyl-3,4-dihydro-2-pyridinone-5-carboxylic acid{3-[4-(4-fluorophenyl)-4-cyano-piperidine-1-yl]-propyl}amide;
4-(S)-(3,4-difluorophenyl)-6-methyl-3,4-dihydro-2-pyridinone-5-carboxylic acid{3-[4-(4-fluorophenyl)-4-cyano-piperidine-1-yl]-propyl}amide;
4-(R)-(3,4-difluorophenyl)-1,6-dimethyl-3,4-dihydro-2-pyridinone-5-carboxylic acid{3-[4-(4-fluorophenyl)-4-cyano-piperdine-1-yl]-propyl}amide;
4-(S)-(3,4-difluorophenyl)-1,6-dimethyl-3,4-dihydro-2-pyridinone-5-carboxylic acid{3-[4-(4-fluorophenyl)-4-cyano-piperidine-1-yl]-propyl}amide;
4-(R)-(3,4-difluorophenyl)-6-methyl-3,4-dihydro-2-pyridinone-5-carboxylic acid{3-[4-(2-cyano-4-fluorophenyl)-4-cyano-piperidine-1-yl]-propyl}amide;
4-(R)-(3,4-difluorophenyl)-1,6-dimethyl-3,4-dihydro-2-pyridinone-5-carboxylic acid{3-[4-(2-cyano-4-fluorophenyl)-4-cyano-piperidine-1-yl]-propyl}amide;
4-(R)-(3,4-difluorophenyl)-6-methyl-3,4-dihydro-2-pyridinone-5-carboxylic acid{3-[4-(2,4-difluorophenyl)-4-cyano-piperidine-1-yl]-propyl}amide;
4-(S)-(3,4-difluorophenyl)-6-methyl-3,4-dihydro-2-pyridinone-5-carboxylic acid{3-[4-(2,4-difluorophenyl)-4-cyano-piperidine-1-yl]-propyl}amide;
4-(R)-(3,4-difluorophenyl)-1,6-dimethyl-3,4-dihydro-2-pyridinone-5-carboxylic acid{3-[4-(2,4-difluorophenyl)-4-cyano-piperidine-1-yl]-propyl}amide;
4-(S)-(3,4-difluorophenyl)-1,6-dimethyl-3,4-dihydro-2-pyridinone-5-carboxylic acid{3-[4-(2,4-difluorophenyl)-4-cyano-piperidine-1-yl]-propyl}amide;
4-(R)-(3,4-difluorophenyl)-6-methyl-3,4-dihydro-2-pyridinone-5-carboxylic acid{3-[4-(2-cyanophenyl)-piperidine-1-yl]-propyl}amide;
4-(R)-(3,4-difluorophenyl)-1,6-dimethyl-3,4-dihydro-2-pyridinone-5-carboxylic acid{3-[4-(2-cyanophenyl)-piperidine-1-yl]-propyl}amide;
4-(R)-(3,4-difluorophenyl)-6-methyl-3,4-dihydro-2-pyridinone-5-carboxylic acid{3-[4-(2-cyanophenyl)-4-cyano-piperidine-1-yl]-propyl}amide;
4-(R)-(3,4-difluorophenyl)-1,6-dimethyl-3,4-dihydro-2-pyridinone-5-carboxylic acid{3-[4-(2-cyanophenyl)-4-cyano-piperidine-1-yl]-propyl}amide; and pharmaceutically acceptable salts thereof.

Another example of the invention is a compound selected from the group consisting of:
4-(R)-(3,4-difluorophenyl)-6-methyl-3,4-dihydro-2-pyridinone-5-carboxylic acid{3-[4-(2-cyano-4-fluorophenyl)-piperidine-1-yl]-propyl}amide, which has the formula:

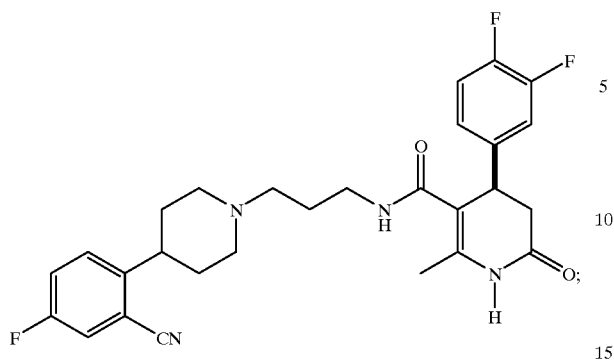

4-(R)-(3,4-difluorophenyl)-1,6-dimethyl-3,4-dihydro-2-pyridinone-5-carboxylic acid{3-[4-(2-cyano-4-fluorophenyl)-piperidine-1-yl]-propyl}amide, which has the formula:

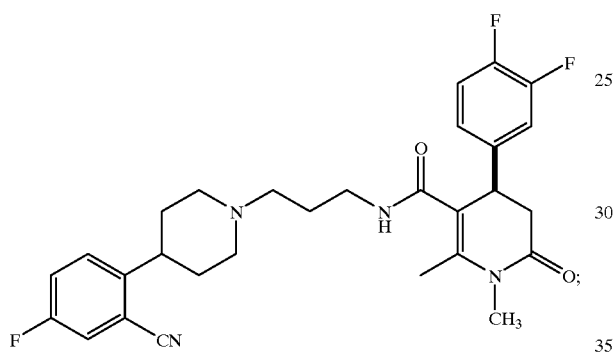

and pharmaceutically acceptable salts thereof.

Still another example of the invention is 4-(R)-(3,4-difluorophenyl)-1,6-dimethyl-3,4-dihydro-2-pyridinone-5-carboxylic acid{3-[4-(2-cyano-4-fluorophenyl)-piperidine-1-yl]-propyl}amide, which has the formula:

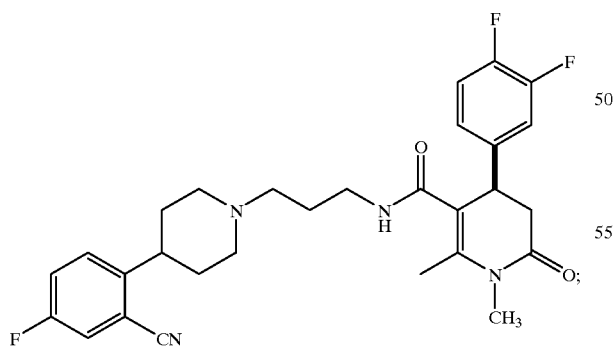

or a pharmaceutically acceptable salt thereof.

In still another sub-class of the first class is a compound of Formula (IIb):

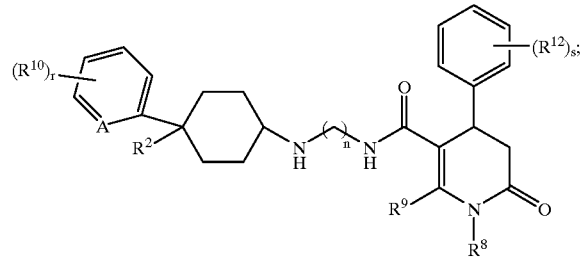

wherein
A is $CR^{10}$ or N;
$R^2$ is hydrogen, cyano, hydroxy, or methoxy;
$R^8$ is hydrogen or methyl;
$R^9$ is hydrogen or methyl;
each $R^{10}$ is independently selected hydrogen, fluoro, cyano, hydroxy, methyl, methoxy, $CF_3$, or $OCF_3$; and
provided that when $R^2$ is hydrogen and A is $CR^{10}$ wherein $R^{10}$ is hydrogen, the other $R^{10}$ is neither fluoro nor $CF_3$;
or a pharmaceutically acceptable salt thereof.

In one aspect, the compound of Formula (IIb) is a (+) enantiomer or a pharmaceutically acceptable salt thereof. In another aspect, the compound of Formula (IIb) is a (−) enantiomer or a pharmaceutically acceptable salt thereof.

In a second class of the invention is a compound of Formula (III):

(III)

wherein
A is $CR^{10}$ or N;
$R^2$ is hydrogen, cyano, hydroxy, $C_1$–$C_6$ alkoxy, $CO_2R^c$, $C(=O)N(R^c)_2$, phenyl, or mono- or poly-substituted phenyl; wherein each of the substituents on the substituted phenyl is independently selected from halo, cyano, nitro, hydroxy, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, and $(CH_2)_{0-4}SO_2R^c$;
$R^8$ is hydrogen, $C_1$–$C_4$ alkyl, $(CH_2)_{0-4}CO_2R^c$, or $(CH_2)_{0-4}C(=O)R^c$;
$R^9$ is hydrogen, halo, cyano, $C_1$–$C_6$ alkyl, $C_3$–$C_6$ cycloalkyl, $C_1$–$C_6$ alkoxy, halogenated $C_1$–$C_6$ alkyl, halogenated $C_1$–$C_6$ alkoxy, $(CH_2)_{1-4}OR^b$, $CO_2R^c$, $C(=O)R^c$, or $C(=O)N(R^c)_2$;

$R^{10}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

$R^{12}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

$R^a$ is hydrogen, $C_1$–$C_6$ alkyl, or halogenated $C_1$–$C_6$ alkyl;

$R^b$ is hydrogen, $C_1$–$C_6$ alkyl, or halogenated $C_1$–$C_6$ alkyl;

$R^c$ and $R^d$ are each independently selected from hydrogen, $C_1$–$C_6$ alkyl, $C_3$–$C_8$ cycloalkyl and $(CH_2)_{1-4}CF_3$;

n is an integer of from 1 to 4; and r and s are independently integers of from 0 to 2;

or a pharmaceutically acceptable salt thereof.

In one aspect, the compound of Formula (III) is a (+) enantiomer or a pharmaceutically acceptable salt thereof. In another aspect, the compound of Formula (III) is a (−) enantiomer or a pharmaceutically acceptable salt thereof. In yet another aspect, in the compound of Formula (III), n is an integer of from 2 to 4, and all other variables are as originally defined for the second class; or a pharmaceutically acceptable salt thereof.

In a sub-class of the second class is a compound of Formula (III), wherein $R^2$ is hydrogen, cyano, hydroxy, $C_1$–$C_4$ alkoxy, $CO_2R^c$, $C(=O)N(R^c)_2$, phenyl, or mono- or poly-substituted phenyl; wherein each of the substituents on the substituted phenyl is independently selected from halo, cyano, hydroxy, $C_1$–$C_4$ alkyl, halogenated $C_1$–$C_4$ alkyl, $C_1$–$C_4$ alkoxy, halogenated $C_1$–$C_4$ alkoxy, $CO_2R^c$, $C(=O)N(R^c)_2$, $N(R^c)_2$, $NR^cC(=O)R^d$, $NR^cC(=O)N(R^d)_2$, $NR^cSO_2R^d$, $SO_2N(R^c)_2$, and $SO_2R^c$;

$R^8$ is hydrogen, $C_1$–$C_4$ alkyl, $CO_2R^c$, or $C(=O)R^c$;

$R^9$ is hydrogen, halo, cyano, $C_1$–$C_4$ alkyl, $C_3$–$C_6$ cycloalkyl, $C_1$–$C_4$ alkoxy, halogenated $C_1$–$C_4$ alkyl, halogenated $C_1$–$C_4$ alkoxy, $(CH_2)_{1-4}OR^b$, $CO_2R^c$, $C(=O)R^c$, or $C(=O)N(R^c)_2$;

$R^{10}$ is hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

$R^{12}$ is hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

$R^a$ is hydrogen, $C_1$–$C_4$ alkyl, or halogenated $C_1$–$C_4$ alkyl;

$R^b$ is hydrogen, $C_1$–$C_4$ alkyl, or halogenated $C_1$–$C_4$ alkyl;

$R^c$ and $R^d$ are each independently selected from hydrogen and $C_1$–$C_4$ alkyl;

and all other variables are as originally defined above for the second class;

or a pharmaceutically acceptable salt thereof.

In one aspect of the preceding sub-class, $R^2$ is hydrogen, cyano, hydroxy, $C_1$–$C_4$ alkoxy, $CO_2R^c$, or $C(=O)N(R^c)_2$;

and all other variables are as defined in the sub-class;

or a pharmaceutically acceptable salt thereof.

In a further aspect of the preceding sub-class, n is an integer of from 2 to 4; and all other variables are as defined in the sub-class; or a pharmaceutically acceptable salt thereof.

Further exemplifying the invention is a compound selected from the group consisting of:

4-(R)-(3,4-difluorophenyl)-6-methyl-3,4-dihydro-2-pyridinone-5-carboxylic acid{2-[4-(2-cyanophenyl)-cyclohexylamine-N-yl]-ethyl}amide;

4-(S)-(3,4-difluorophenyl)-6-methyl-3,4-dihydro-2-pyridinone-5-carboxylic acid{2-[4-(2-cyanophenyl)-cyclohexylamine-N-yl]-ethyl}amide;

4-(R)-(3,4-difluorophenyl)-1,6-dimethyl-3,4-dihydro-2-pyridinone-5-carboxylic acid{2-[4-(2-cyanophenyl)-cyclohexylamine-N-yl]-ethyl}amide; and pharmaceutically acceptable salts thereof.

The present invention also includes a pharmaceutical composition comprising a therapeutically effective amount of any of the compounds described above and a pharmaceutically acceptable carrier. In one embodiment is a pharmaceutical composition made by combining any of the compounds described above and a pharmaceutically acceptable carrier. The present invention further includes a process for making a pharmaceutical composition comprising combining any of the compounds described above and a pharmaceutically acceptable carrier.

The present invention further includes a pharmaceutical composition as described in the preceding paragraph further comprising a therapeutically effective amount of a testosterone 5-alpha reductase inhibitor. In one embodiment, the testosterone 5-alpha reductase inhibitor is a type 1, a type 2, both a type 1 and a type 2 (i.e., a three component combination comprising any of the compounds described above combined with both a type 1 testosterone 5-alpha reductase inhibitor and a type 2 testosterone 5-alpha reductase inhibitor), or a dual type 1 and type 2 testosterone 5-alpha reductase inhibitor. In another embodiment, the testosterone 5-alpha reductase inhibitor is a type 2 testosterone 5-alpha reductase inhibitor. The testosterone 5-alpha reductase inhibitor is suitably finasteride.

The present invention also includes a method of treating benign prostatic hyperplasia in a subject in need thereof which comprises administering to the subject a therapeutically effective amount of any of the compounds (or any of the compositions) described above. In one embodiment of the method of treating BPH, the compound (or composition) does not cause a fall in blood pressure at dosages effective to alleviate BPH. In another embodiment of the method of treating BPH, the compound is administered in combination with a testosterone 5-alpha reductase inhibitor. A suitable testosterone 5-alpha reductase inhibitor for use in the method is finasteride.

The present invention also includes a method of inhibiting contraction of prostate tissue or relaxing lower urinary tract tissue in a subject in need thereof which comprises administering to the subject a therapeutically effective amount of any of the compounds (or any of the compositions) described above. In one embodiment of the method of inhibiting contraction of prostate tissue or relaxing lower urinary tract tissue, the compound (or composition) additionally does not cause a fall in blood pressure at dosages effective to inhibit contraction of prostate tissue. In another embodiment, the compound is administered in combination with a testosterone 5-alpha reductase inhibitor; the testosterone 5-alpha reductase inhibitor is suitably finasteride.

The present invention also includes a method of treating a disease which is susceptible to treatment by antagonism of the alpha 1a receptor which comprises administering to a subject in need thereof an amount of any of the compounds described above effective to treat the disease. Diseases which are susceptible to treatment by antagonism of the alpha 1a receptor include, but are not limited to, BPH, high intraocular pressure, high cholesterol, impotency, sympathetically mediated pain, migraine (see K. A. Vatz, *Headache*, Vol. 37, 107–108 (1997)) and cardiac arrhythmia.

The present invention also includes the use of any of the compounds described above in the preparation of a medicament for: a) treating benign prostatic hyperplasia; b) relaxing lower urinary tract tissue; or c) inhibiting contraction of prostate tissue; in a subject in need thereof.

The present invention further includes the use of any of the alpha 1a antagonist compounds described above and a 5-alpha reductase inhibitor for the manufacture of a medicament for: a) treating benign prostatic hyperplasia; b) relaxing lower urinary tract tissue; or c) inhibiting contraction of prostate tissue which comprises an effective amount of the alpha 1a antagonist compound and an effective amount of 5-alpha reductase inhibitor, together or separately.

As used herein, the term "$C_1$–$C_6$ alkyl" means linear or branched chain alkyl groups having from 1 to 6 carbon atoms and includes all of the hexyl alkyl and pentyl alkyl isomers as well as n-, iso-, sec- and t-butyl, n- and isopropyl, ethyl and methyl. "$C_1$–$C_4$ alkyl" means n-, iso-, sec- and t-butyl, n- and isopropyl, ethyl and methyl.

The term "$C_1$–$C_6$ alkoxy" means an —O-alkyl group wherein alkyl is $C_1$ to $C_6$ alkyl. "$C_1$–$C_4$ alkoxy" has an analogous meaning; i.e., it is an alkoxy group selected from methoxy, ethoxy, n-propoxy, isopropoxy, n-butoxy, isobutoxy, tert-butoxy, and sec-butoxy.

The term "$C_3$–$C_8$ cycloalkyl" means a cyclic ring of an alkane having three to eight total carbon atoms (i.e., cyclopropyl, cyclobutyl, cyclopentyl, cyclohexyl, cycloheptyl or cyclooctyl). "$C_3$–$C_6$ cycloalkyl" refers to a cyclic ring selected from cyclopropyl, cyclobutyl, cyclopentyl, and cyclohexyl.

The term "halo" (which may alternatively be referred to as "halogen") refers to fluoro, chloro, bromo, and iodo (alternatively fluorine, chlorine, bromine and iodine).

The term "halogenated $C_1$–$C_6$ alkyl" (which may altenatively be referred to as "$C_1$–$C_6$ haloalkyl") means a $C_1$ to $C_6$ linear or branched alkyl group as defined above with one or more halogen substituents. The term "halogenated $C_1$–$C_4$ alkyl" has an analogous meaning. Representative examples of suitable haloalkyls include the series $(CH_2)_{0-4}CF_3$ (i.e., trifluoromethyl, 2,2,2-trifluoroethyl, 3,3,3-trifluoro-n-propyl, etc.), tribromomethyl, 1-fluoroethyl, 2-fluoroethyl, 2,2-difluoroethyl 2-bromoethyl, 3,3,3-trifluoroisopropyl, 1,1,1,3,3,3-hexafluoroisopropyl, and perfluorohexyl.

The term "halogenated $C_3$–$C_8$ cycloalkyl" (which may altenatively be referred to as "$C_3$–$C_8$ halocycloalkyl") means a cycloalkyl group as defined above with one or more halogen substituents. "Halogenated $C_3$–$C_6$ cycloalkyl" has an analogous meaning. Representative examples of suitable halocycloalkyls include all isomers of fluorocyclohexyl (i.e., 1-, 2-, 3-, and 4-fluorocyclohexyl), difluorocyclohexyl (e.g., 2,4-difluorocyclohexyl, 3,4-difluorocyclohexyl, etc.), bromocyclohexyl, fluorocyclopentyl, and so forth.

The term "halogenated $C_1$–$C_6$ alkoxy" (which may altenatively be referred to as "$C_1$–$C_6$ haloalkoxy") means a $C_1$–$C_6$ alkoxy group as defined above wherein the alkyl moiety has one or more halogen substituents. "Halogenated $C_1$–$C_4$ alkoxy" has an analogous meaning. Representative examples include the series $O(CH_2)_{0-4}CF_3$ (i.e., trifluoromethoxy, 2,2,2-trifluoroethoxy, 3,3,3-trifluoro-n-propoxy, etc.), chloromethoxy, chloroethoxy, 1,1,1,3,3,3-hexafluoroisopropoxy, and so forth.

The term "heterocyclic" (which may alternatively be referred to as "heterocycle") refers to pyridyl, pyrazinyl, thienyl, thiazolyl, furanyl and quinazolyl. The heterocyclic ring may be attached at any heteroatom or carbon atom which results in the creation of a stable structure.

The term "thienyl," as used herein, refers to the group

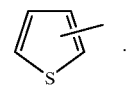

The term "aryl" refers to phenyl, substituted phenyl, naphthyl, and substituted naphthyl.

The term "heteroaryl" refers to heterocyclic or substituted heterocyclic.

The term "substituted" includes mono- and poly-substitution by a named substituent to the extent such single and multiple substitution is chemically allowed.

The term "poly-substituted" refers herein to multiple degrees of substitution by a named substituent or substituents. For example, the term "poly-substituted phenyl" denotes di-, tri-, tetra- and penta-substitution by a named substituent or a combination of named substituents (e.g., "di-substituted phenyl wherein each substituent is independently selected from fluoro, rnethoxy and cyano" represents such moieties as 2,4-difluorophenyl, 3,4-difluorophenyl, 2-methoxy-4-fluorophenyl, 2-fluoro-4-cyanophenyl, 2-cyano-4-fluorophenyl, 3-cyano-4-fluorophenyl, etc.)

It is understood that the definition of a substituent (e.g., $(CH_2)_{0-4}CO_2R^c$) or variable (e.g., $R^c$) at a particular location in a molecule is independent of its definitions at other locations in that molecule. Thus, for example, when $R^1$ is mono-substituted phenyl wherein the substituent is $(CH_2)_{0-4}CO_2R^c=CO_2H$, and $R^7$ is also mono-substituted phenyl wherein the substituent is $(CH_2)_{0-4}CO_2R^c$, it is understood that the substituent on the phenyl in $R^7$ can be any one of $CO_2H$, $CO_2Me$, $CO_2Et$, $CO_2Pr$, $CH_2CO_2H$, $CH_2CO_2Me$, $CH_2CO_2Et$, $CH_2CO_2Pr$, $(CH_2)_2CO_2H$, etc. As another example, the moiety

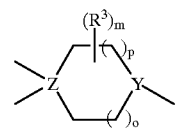

wherein $R^3$ is $C_1$–$C_4$ alkyl, m=2, o=1, and p=1, represents moieties such as

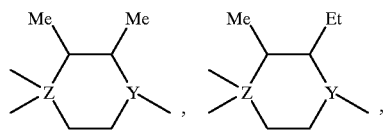

-continued

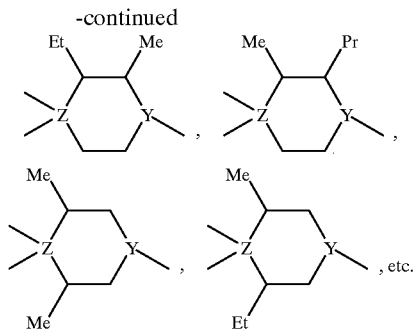

It is also understood that the definition of a substituent or variable at a particular location in a molecule is independent of the definition of another occurrence of the same substituent or variable at the same location. Thus, $C(=O)N(R^c)_2$ represents groups such as $-C(=O)NH_2$, $-C(=O)NHMe$, $-C(=O)NHEt$, $-C(=O)NMe_2$, $-C(=O)N(Me)Et$, etc.

It is understood that substituents and substitution patterns on the compounds of the instant invention can be selected by one of ordinary skill in the art to provide compounds that are chemically stable and that can be readily synthesized by the methods set forth below and, when viewed in the light of this disclosure, by techniques known in the art. Where multiple substituent moieties are disclosed or claimed, the substituted compound can be independently substituted by one or more of the disclosed or claimed substituent moieties, singly or plurally.

Other embodiments for the variables and substituents set forth in Formula (I) include the following:

$R^1$ is phenyl, mono- or poly-substituted phenyl, pyridyl, or mono- or poly-substituted pyridyl; or is phenyl, mono- or di-substituted phenyl, pyridyl, or mono- or di-substituted pyridyl. In still other embodiments, $R^1$ is phenyl, or mono- or di-substituted phenyl; or is pyridyl, or mono- or di-substituted pyridyl.

When $R^1$ is substituted phenyl, each of the substituents is independently selected from halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; or is selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$. In still other embodiments, each of the substituents is independently selected from halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, and $(CH_2)_{1-4}OR^a$; or is selected from fluoro, cyano, hydroxy, $C_1$–$C_4$ alkyl, $(CH_2)_{0-3}CF_3$, $OCF_3$, and $(CH_2)_{1-3}OCF_3$.

When $R^1$ is substituted pyridyl, each of the substituents is independently selected from halo, cyano, nitro, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl, $C_1$–$C_4$ alkyl, halogenated $C_1$–$C_4$ alkyl, $C_1$–$C_4$ alkoxy, halogenated $C_1$–$C_4$ alkoxy, $(CH_2)_{1-4}OR^a$, $C_3$–$C_6$ cycloalkyl, and halogenated $C_3$–$C_6$ cycloalkyl; or is independently selected from halo, cyano, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1$–$C_4$ alkyl, halogenated $C_1$–$C_4$ alkyl, $C_1$–$C_4$ alkoxy, halogenated $C_1$–$C_4$ alkoxy, and $(CH_2)_{1-4}OR^a$. In still other embodiments, each of the substituents is independently selected from halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, and $(CH_2)_{1-4}OR^a$; or is selected from fluoro, cyano, hydroxy, $C_1$–$C_4$ alkyl, $(CH_2)_{0-3}CF_3$, $OCF_3$, and $(CH_2)_{1-3}OCF_3$.

In yet another embodiment, $R^1$ is

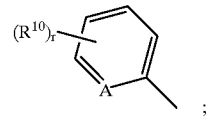

wherein A is $C$-$R^{10}$ or N; $R^{10}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$; and r is an integer of from 0 to 2.

$R^2$ is hydrogen, cyano, hydroxy, $C_1$–$C_6$ alkoxy, $CO_2R^c$, $C(=O)N(R^c)_2$, tetrazole, isooxadiazole, phenyl, mono- or poly-substituted phenyl, pyridyl, or mono- or poly-substituted pyridyl; or is hydrogen, cyano, hydroxy, $C_1$–$C_6$ alkoxy, $CO_2R^c$, $C(=O)N(R^c)_2$, tetrazole, isooxadiazole, phenyl, mono- or di-substituted phenyl, or mono- or di-substituted pyridyl; or is hydrogen, cyano, hydroxy, $C_1$–$C_6$ alkoxy, $CO_2R^c$, $C(=O)N(R^c)_2$, tetrazole, isooxadiazole, or phenyl. In still other embodiments, $R^2$ is hydrogen, cyano, hydroxy, $C_1$–$C_6$ alkoxy, $CO_2R^c$, $C(=O)N(R^c)_2$, tetrazole, or isooxadiazole; or is hydrogen, cyano, hydroxy, $C_1$–$C_6$ alkoxy, $CO_2R^c$, or $C(=O)N(R^c)_2$.

When $R^2$ is substituted phenyl, each of the substituents is independently selected from halo, cyano, nitro, hydroxy, $C_1$–$C_4$ alkoxy, halogenated $C_1$–$C_4$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, $(CH_2)_{0-4}SO_2R^c$, $C_1$–$C_4$ alkyl, halogenated $C_1$–$C_4$ alkyl, $C_3$–$C_6$ cycloalkyl, and halogenated $C_3$–$C_6$ cycloalkyl; or is independently selected from halo, cyano, hydroxy, $C_1$–$C_4$ alkoxy, halogenated $C_1$–$C_4$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, $(CH_2)_{0-4}SO_2R^c$, $C_1$–$C_4$ alkyl, and halogenated $C_1$–$C_4$ alkyl; or is independently selected from fluoro, cyano, hydroxy, $C_1$–$C_4$ alkyl, $(CH_2)_{0-3}CF_3$, $OCF_3$, and $(CH_2)_{1-3}OCF_3$.

When $R^2$ is substituted pyridyl, each of the substituents is independently selected from halo, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl, $C_1$–$C_4$ alkyl, halogenated $C_1$–$C_4$ alkyl, $C_1$–$C_4$ alkoxy, halogenated $C_1$–$C_4$ alkoxy, $(CH_2)_{1-4}OR^a$, $C_3$–$C_6$ cycloalkyl, and halogenated $C_3$–$C_6$ cycloalkyl; or is independently selected from halo, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1$–$C_4$ alkyl, halogenated $C_1$–$C_4$ alkyl, $C_1$–$C_4$ alkoxy, halogenated $C_1$–$C_4$ alkoxy, and $(CH_2)_{1-4}OR^a$.

$R^3$ is methyl, ethyl, n-propyl, or isopropyl; or is methyl or ethyl.

$R^4$ and $R^5$ are each independently selected from hydrogen and $C_1$–$C_4$ alkyl. In other embodiments, $R^4$ and $R^5$ are both hydrogen; or one of $R^4$ and $R^5$ is hydrogen and the other is hydrogen or $C_1$–$C_4$ alkyl. In still another embodiment, $R^4$ and $R^5$ together with the carbon atom to which they are attached form methylene ($-CH_2-$) units or alkylidene units of formula (—CR'H—) wherein R' is $C_1$–$C_4$ alkyl or, in cases where there are at least two $CR^4R^5$'s (e.g., when n=2), mixtures of the foregoing units.

$R^6$ is hydrogen, methyl, or ethyl; or is hydrogen.

$R^7$ is phenyl, or mono- or di-substituted phenyl; or is mono- or di-substituted phenyl.

When $R^7$ is substituted phenyl, each of the substituents is independently selected from halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR_cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; or is independently selected from halo, cyano, hydroxy, $C_1$–$C_4$ alkyl $C_1$–$C_4$ alkoxy, halogenated $C_1$–$C_4$ alkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; or is independently selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, and $SO_2R^c$. In other embodiments, each of the substituents is independently selected from halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, and $(CH_2)_{1-4}OR^b$; or is selected from fluoro, cyano, hydroxy, $C_1$–$C_4$ alkyl, $(CH_2)_{0-3}CF_3$, $OCF_3$, and $(CH_2)_{1-3}OCF_3$.

In still another embodiment, $R^7$ is

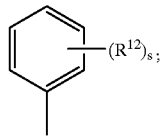

wherein $R^{12}$ is hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$; and s is an integer of from 0 to 2.

$R^8$ is hydrogen, $C_1$–$C_4$ alkyl, $(CH_2)_{0-4}CO_2R^c$, or $(CH_2)_{0-4}C(=O)R^c$; or is hydrogen, $C_1$–$C_4$ alkyl, $CO_2R^c$, or $C(=O)R^c$.

$R^9$ is hydrogen, halo, cyano, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $CO_2R^c$, $C(=O)R^c$, or $C(=O)N(R^c)_2$; or is hydrogen, halo, cyano, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^b$, $CO_2R^c$, $C(=O)R^c$, or $C(=O)N(R^c)_2$. In still another embodiment, $R^9$ is hydrogen, halo, cyano, $C_1$–$C_4$ alkyl, $C_1$–$C_4$ alkoxy, $(CH_2)_{0-3}CF_3$, $OCF_3$, $(CH_2)_{1-3}OCF_3$, $CO_2R^c$, $C(=O)R^c$, or $C(=O)N(R^c)_2$.

Each of $R^a$ and $R^b$ is independently hydrogen, $C_1$–$C_4$ alkyl, or halogenated $C_1$–$C_4$ alkyl; or is $C_1$–$C_4$ alkyl or halogenated $C_1$–$C_4$ alkyl; or is $C_1$–$C_4$ alkyl or $(CH_2)_{0-3}CF_3$. In another embodiment, each of $R^a$ and $R^b$ is independently hydrogen, methyl, ethyl, $CF_3$, or $CH_2CF_3$.

$R^c$ and $R^d$ are each independently selected from hydrogen, $C_1$–$C_4$ alkyl, $C_3$–$C_6$ cycloalkyl and $(CH_2)_{1-4}CF_3$; or are each independently selected from hydrogen, $C_1$–$C_4$ alkyl, and $(CH_2)_{1-4}CF_3$. In still another embodiment, $R^c$ and $R^d$ are each independently selected from hydrogen, methyl, ethyl, $CF_3$, and $CH_2CF_3$.

Halo is fluoro or bromo; or is fluoro.

m is 0 or 1; or is 0.

n is an integer of from 2 to 4, when X is $NR^6$; or n is 3, when X is $NR^6$.

n is an integer of from 1 to 3, when X is $CR^4R^5$; or n is 2, when X is $CR^4R^5$.

o is an integer equal to 1; or is an integer equal to 0 or 1, provided that when Y is N, o is zero.

p and q are each integers of from 0 to 2, wherein the sum of p+q is 2; i.e., p=1 and q=1, or p=0 and q=2, or p=2 and q=0.

Representative compounds of the present invention exhibit high selectivity for the human alpha 1a adrenergic receptor. One implication of this selectivity is that these compounds display selectivity for lowering intraurethral pressure without substantially affecting diastolic blood pressure.

Representative compounds of this invention display submicromolar affinity for the human alpha 1a adrenergic receptor subtype while typically displaying at least about ten-fold lower affinity for the human alpha 1d and alpha 1b adrenergic receptor subtypes, and many other G-protein coupled human receptors. Particular representative compounds of this invention exhibit nanomolar and subnanomolar affinity for the human alpha 1a adrenergic receptor subtype while displaying at least about 30 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors). Still other representative compounds of this invention exhibit nanomolar and subnanomolar affinity for the human alpha 1a adrenergic receptor subtype while displaying at least about 100 fold lower affinity for the human alpha 1d and alpha 1b adrenergic receptor subtypes, and many other G-protein coupled human receptors (e.g., serotonin, dopamine, alpha 2 adrenergic, beta adrenergic or muscarinic receptors).

These compounds are administered in dosages effective to antagonize the alpha 1a receptor where such treatment is needed; e.g., treatment of BPH. For use in medicine, the salts of the compounds of this invention refer to non-toxic "pharmaceutically acceptable salts." Other salts may, however, be useful in the preparation of the compounds according to the invention or in the prepartion of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quatemary ammonium salts. Thus, representative pharmaceutically acceptable salts include the following:

Acetate, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Compounds of this invention are used to reduce the acute symptoms of BPH. Thus, compounds of this invention may be used alone or in combination with more long-term anti-BPH therapeutics, such as testosterone 5-a reductase inhibitors, including PROSCAR® (finasteride). Aside from their utility as anti-BPH agents, these compounds may be used to induce highly tissue-specific, localized alpha 1a adrenergic receptor blockade whenever this is desired. Effects of this blockade include reduction of intra-ocular pressure, control of cardiac arrhythmias, and possibly a host of alpha 1a receptor mediated central nervous system events.

The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in Design of Prodrugs, ed. H. Bundgaard, Elsevier, 1985. Metabolites of these compounds include active species produced upon introduction of compounds of this invention into the biological milieu.

Where the compounds according to the invention have at least one chiral center, they may accordingly exist as enantiomers. Where the compounds according to the invention possess two or more chiral centers, they may additionally exist as diastereoisomers. It is to be understood that all such isomers and mixtures thereof are encompassed within the scope of the present invention. Furthermore, some of the crystalline forms for compounds of the present invention may exist as polymorphs and as such are intended to be included in the present invention. In addition, some of the compounds of the present invention may form solvates with water (i.e., hydrates) or common organic solvents. Such solvates are also encompassed within the scope of this invention.

The term "selective alpha 1a adrenergic receptor antagonist," as used herein, refers to an alpha 1a antagonist compound which exhibits selectivity (e.g., at least about ten fold selective) for the human alpha 1a adrenergic receptor as compared to the human alpha 1b, alpha 1d, alpha 2a, alpha 2b and alpha 2c adrenergic receptors.

The term "lower urinary tract tissue," as used herein, refers to and includes, but is not limited to, prostatic smooth muscle, the prostatic capsule, the urethra and the bladder neck.

The term "subject," as used herein refers to an animal, preferably a mammal, most preferably a human, who has been the object of treatment, observation or experiment.

The term "therapeutically effective amount" as used herein means that amount of active compound or pharmaceutical agent that elicits the biological or medicinal response in a tissue, system, animal or human that is being sought by a researcher, veterinarian, medical doctor or other clinician, which includes alleviation of the symptoms of the disease being treated.

The present invention includes pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

As used herein, the term "composition" encompasses a product comprising the specified ingredients in the specified amounts, as well as any product which results, directly or indirectly, from combination of the specified ingredients in the specified amounts.

The liquid forms in which the novel compositions of the present invention may be incorporated for administration orally or by injection include aqueous solutions, suitably flavoured syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Where the processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

The specificity of binding of compounds showing affinity for the alpha 1a receptor is shown by comparing affinity to membranes obtained from transfected cell lines that express the alpha 1a receptor and membranes from cell lines or tissues known to express other types of alpha (e.g., alpha 1d, alpha 1b) or beta adrenergic receptors. Expression of the cloned human alpha 1 d, alpha 1b, and alpha 1a receptors and comparison of their binding properties with known selective antagonists provides a rational way for selection of compounds and discovery of new compounds with predictable pharmacological activities. Antagonism by these compounds of the human alpha 1a adrenergic receptor subtype may be functionally demonstrated in anesthetized animals. These compounds may be used to increase urine flow without exhibiting hypotensive effects.

The ability of compounds of the present invention to specifically bind to the alpha 1a receptor makes them useful for the treatment of BPH. The specificity of binding of compounds showing affinity for the alpha 1a receptor is compared against the binding affinities to other types of alpha or beta adrenergic receptors. The human alpha adrenergic receptor of the 1a subtype was recently identified, cloned and expressed as described in PCT International Application Publication Nos. WO94/08040, published Apr. 14, 1994 and WO 94/21660, published Sep. 29, 1994. The cloned human alpha 1a receptor, when expressed in mammalian cell lines, is used to discover ligands that bind to the receptor and alter its function. Expression of the cloned human alpha 1d, alpha 1b, and alpha 1a receptors and comparison of their binding properties with known selective antagonists provides a rational way for selection of compounds and discovery of new compounds with predictable pharmacological activities.

Compounds of this invention exhibiting human alpha 1a adrenergic receptor antagonism may further be defined by counterscreening. This is accomplished according to methods known in the art using other receptors responsible for mediating diverse biological functions. [See e.g. PCT International Application Publication No. WO94/10989, published May 26, 1994; U.S. Pat. No. 5,403,847, issued Apr. 4, 1995]. Compounds which are both selective amongst the various human alpha1 adrenergic receptor subtypes and which have low affinity for other receptors, such as the alpha 2 adrenergic receptors, the β-adrenergic receptors, the muscarinic receptors, the serotonin receptors, and others are particularly preferred. The absence of these non-specific activities may be confirmed by using cloned and expressed receptors in an analogous fashion to the method disclosed herein for identifying compounds which have high affinity for the various human alpha1 adrenergic receptors. Furthermore, functional biological tests are used to confirm the effects of identified compounds as alpha 1a adrenergic receptor antagonists.

The present invention also has the objective of providing suitable topical, oral, systemic and parenteral pharmaceutical formulations for use in the novel methods of treatment of the present invention. The compositions containing compounds of this invention as the active ingredient for use in the specific antagonism of human alpha 1a adrenergic receptors can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an alpha 1a antagonistic agent.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacrylamidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

Compounds of this invention may be administered in any of the foregoing compositions and according to dosage regimens established in the art whenever specific blockade of the human alpha 1a adrenergic receptor is required.

The daily dosage of the products may be varied over a wide range; e.g., from about 0.01 to about 1000 mg per adult human per day. For oral administration, the compositions are preferably provided in the form of tablets containing 0.01, 0.05, 0.1, 0.5, 1.0, 2.5, 5.0, 10.0, 15.0, 25.0, 50.0 and 100 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. An effective amount of the drug is ordinarily supplied at a dosage level of from about 0.0002 mg/kg to about 20 mg/kg of body weight per day. Preferably, the range is from about 0.001 to about 10 mg/kg of body weight per day, and especially from about 0.001 mg/kg to about 7 mg/kg of body weight per day. The compounds may be administered on a regimen of 1 to 4 times per day.

Compounds of this patent disclosure may be used alone at appropriate dosages defined by routine testing in order to obtain optimal antagonism of the human alpha 1a adrenergic receptor while minimizing any potential toxicity. In addition, co-administration or sequential administration of other agents which alleviate the effects of BPH is desirable. Thus, in one embodiment, this invention is administration of compounds of this invention and a human testosterone 5-a reductase inhibitor. Included with this embodiment are inhibitors of 5-alpha reductase isoenzyme 2. Many such compounds are now well known in the art and include such compounds as PROSCAR®, (also known as finasteride, a 4-Aza-steroid; see U.S. Pat. Nos. 4,377,584 and 4,760,071, for example). In addition to PROSCAR®, which is principally active in prostatic tissue due to its selectivity for human 5-a reductase isozyme 2, combinations of compounds which are specifically active in inhibiting testosterone 5-alpha reductase isozyme 1 and compounds which act as dual inhibitors of both isozymes 1 and 2, are useful in combination with compounds of this invention. Compounds that are active as 5a-reductase inhibitors have been described in WO93/23420, EP 0572166; WO 93/23050; WO93/23038,; WO93/23048; WO93/23041; WO93/23040; WO93/23039; WO93/23376; WO93/23419, EP 0572165; WO93/23051.

The dosages of the alpha 1a adrenergic receptor and testosterone 5-alpha reductase inhibitors are adjusted when combined to achieve desired effects. As those skilled in the art will appreciate, dosages of the 5-alpha reductase inhibitor and the alpha 1a adrenergic receptor antagonist may be independently optimized and combined to achieve a synergistic result wherein the pathology is reduced more than it would be if either agent were used alone. In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Thus, in one embodiment of the present invention, a method of treating BPH is provided which comprises administering to a subject in need of treatment any of the compounds of the present invention in combination with finasteride effective to treat BPH. The dosage of finasteride administered to the subject is from about 0.01 mg per subject per day to about 50 mg per subject per day in combination with an alpha 1a antagonist. In one aspect, the dosage of finasteride in the combination is from about 0.2 mg per subject per day to about 10 mg per subject per day, and, in another aspect, from about 1 to about 7 mg per subject to day (e.g., about 5 mg per subject per day).

For the treatment of benign prostatic hyperplasia, compounds of this invention exhibiting alpha 1a adrenergic receptor blockade can be combined with a therapeutically effective amount of a 5a-reductase 2 inhibitor, such as finasteride, in addition to a 5a-reductase 1 inhibitor, such as 4,7β-dimethyl-4-aza-5a-cholestan-3-one, in a single oral, systemic, or parenteral pharmaceutical dosage formulation. Alternatively, a combined therapy can be employed wherein the alpha 1a adrenergic receptor antagonist and the 5a-reductase 1 or 2 inhibitor are administered in separate oral, systemic, or parenteral dosage formulations. See, e.g., U.S. Pat. No. 4,377,584 and U.S. Pat. No. 4,760,071 which describe dosages and formulations for 5a-reductase inhibitors.

Abbreviations used in the instant specification, particularly the Schemes and Examples, are as follows:

ACN=acetonitrile

AcOH=acetic acid

Bn=benzyl

Boc or BOC=t-butyloxycarbonyl
DMF=N,N-dimethylformamide
DMSO=dimethylsulfoxide
EDC=1-(3-dimethylaminopropyl)-3-ethyl carbodiimide hydrochloride
Et=ethyl
Et$_3$N=triethylamine
EtOAc=ethyl acetate
HOAt=1-hydroxy-7-azabenzotriazole
HPLC=high performance liquid chromatography
LDA=lithium diisopropylamide
Me=methyl
MeOH=methanol
MP=melting point
MS=mass spectrometry
n-BuLi=n-butyllithium
NMR=nuclear magnetic resonance
Pr=propyl
Tf=triflic or triflate
TFA=trifluoroacetic acid
THF=tetrahydrofuran
TLC=thin layer chromatography The compounds of the present invention can be prepared readily according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above.

Many of the compounds claimed within this invention can be assembled via Schemes I and II shown below. Scheme I describes the preparation of amines (4, 6, 8, 12) suitable for the preparation of many of the compounds of the present invention. In Scheme I, part a, 1-Boc-4-piperidone or a substituted analog (1) can be treated with LDA followed by N-triflic amide to provide the corresponding triflate 2. Palladium catalyzed coupling with an aryl or heteroaryl organozincate R$^1$ZnX, followed by hydrogenation of the resulting alkene and nitrogen deprotection with HCl(g) affords a substituted piperidine hydrochloride of type 3. Alkylation with 3-bromo-1-Boc-propylamine in the presence of triethylamine followed by deprotection with HCl(g) affords amine 4. Alkylation with other monoprotected amines of general formula Br(CR$^4$R$^5$)$_n$NHBoc, followed by deprotection allows for the preparation of a diverse range of amines of type 4.

As shown in Scheme I, part b, the piperidone 1 can be reacted with Grignard reagents R$^1$MgX to provide tertiary alcohols of type 5, which can be converted to amines of type 6. Alkylation with other monoprotected amines of general formula Br(CR$^4$R$^5$)$_n$NHBoc, followed by deprotection allows for the preparation of a diverse range of amines of type 6.

As shown in Scheme I, part c, aryl- and heteroaryl-acetonitriles can be treated with a base such as NaH or cesium carbonate and with bis-(2-chloroethyl)-tert-butoxycarbonylamine to afford the piperidine derivatives of type 7. Deprotection and alkylation as described before gives access to amines of type 8. Alkylation with other monoprotected amines of general formula Br(CR$^4$R$^5$)$_n$NHBoc, followed by deprotection allows for the preparation of a diverse range of amines of type 8.

As shown in Scheme I, part d, triflate 10 can readily be prepared from 1,4-cyclohexanedione monoethylene ketal (9) using LDA and triflic amide. Palladium catalyzed coupling with an aryl or heteroaryl organozincate R$^1$ZnX, followed by hydrogenation of the resulting alkene and hydrolysis of the ketal with 1N HCl in dioxane provides ketone 11. Reductive amination of the previous ketone with mono-Boc ethylenediamine followed by deprotection affords cyclohexylamines of type 12. Reductive amination with other monoprotected diamines of general formula H$_2$N(CR$^4$R$^5$)$_n$NHBoc followed by deprotection allows for the preparation of a diverse range of amines of type 12.

Scheme II describes the preparation of dihydropyridinone derivatives 14 and 15 and their coupling to amines 4, 6, 8, 12 as needed for the preparation of many of the compounds of the present invention. Dihydropyridinones 13 can be prepared in racemic form by heterocyclization of arylaldehydes R$^7$CHO and b-ketoesters with Meldrum's acid, according to Seoane's and Svetlik's procedures (*J. Heterocyclic Chem.*, 1996, 33, 103; *J. Chem. Soc. Perkin Trans.* 1, 1996, 947–951; *J. Chem. Soc. Perkin Trans.* 1, 1990, 1315–1318). Hydrogenolysis of the resulting benzyl ester or hydrolysis of alkyl ester provides of dihydropyridinone carboxylic acid derivative 14. Standard amine coupling using EDC/HOAt and the amines 4, 6, 8, and 12 described in Scheme I afford compounds of type 16 as racemates. Chiral preparative HPLC separation provides each enantiomer separately.

Further according to Scheme II, amide 13 can also be alkylated or acylated (R$^8$X, R$^8$COX, R$^8$OCOX) using standard procedures prior to ester hydrogenolysis or hydrolysis, to provide carboxylic acids of type 15. Standard amine coupling using EDC/HOAt and the amines 4, 6, 8, and 12 described in Scheme I afford compounds of type 17 as racemates. Chiral preparative HPLC separation provides each enantiomer separately. Alternatively, esters of type 13 can be resolved by chiral preparative HPLC to allow for the preparation of compounds of type 16 and 17 as single enantiomers directly.

Substituted pyrrolinones (5-membered ring analogs of intermediates 14 and 15) can be prepared from arylglyoxal and enamines according to Caballerro's procedure as described in (*Tetrahedron*, 1994, 50, 7849–7856) and coupled to amines 4, 6, 8, and 12 as needed for the preparation of many of the compounds of the present invention.

Scheme III below outlines the specific procedures set forth in Examples 10–13 for preparing the dihydropyridinone precursors employed in Examples 14–33.

Scheme IV below outlines the specific procedures set forth in Examples 1–9 for preparing the amines employed in Examples 14–33.

SCHEME I
a.
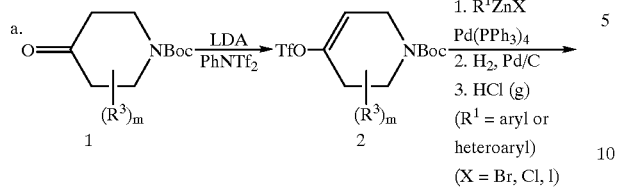
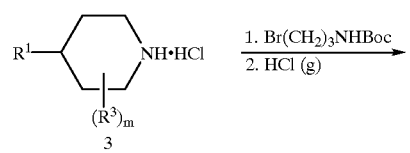
b.
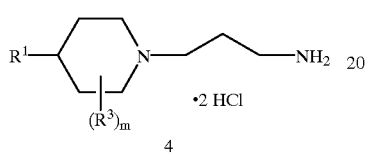
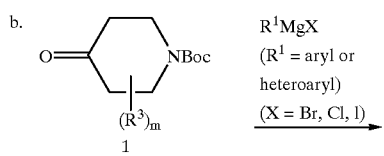
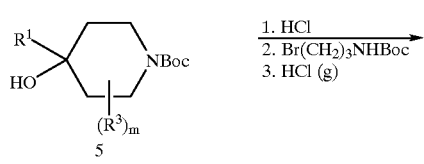
c.
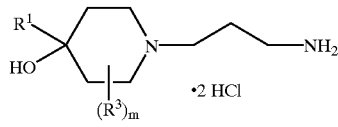
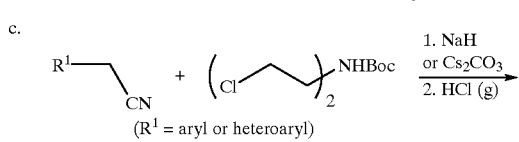
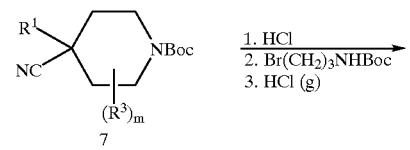
d.
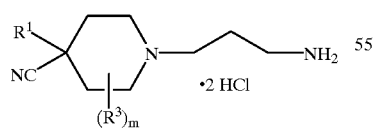
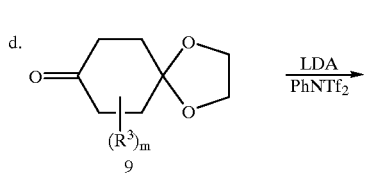
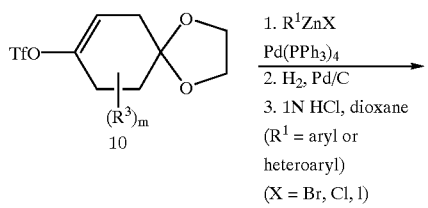
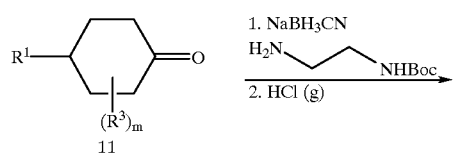
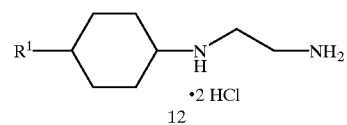
SCHEME II
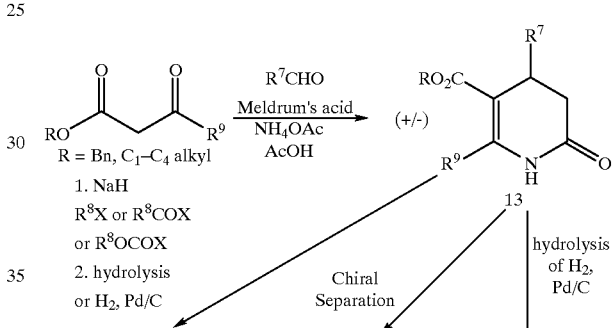
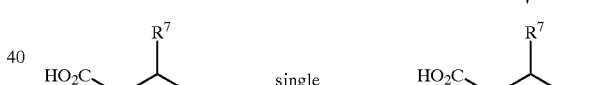
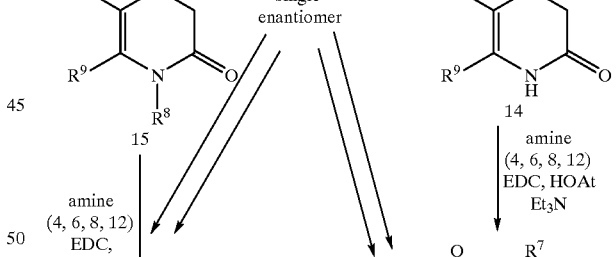
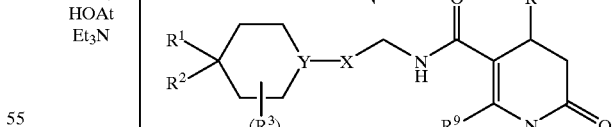
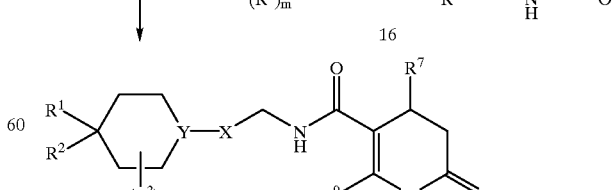

SCHEME III
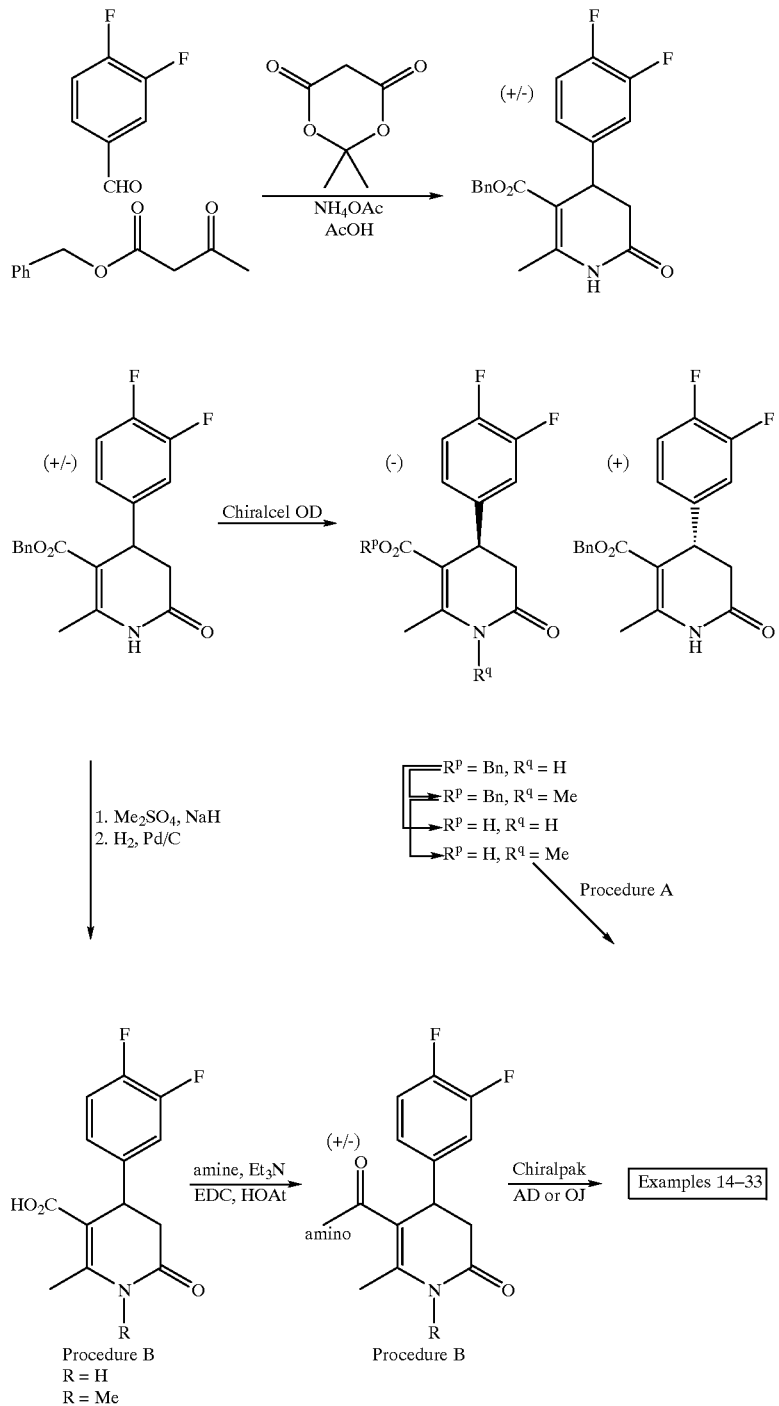

SCHEME IV

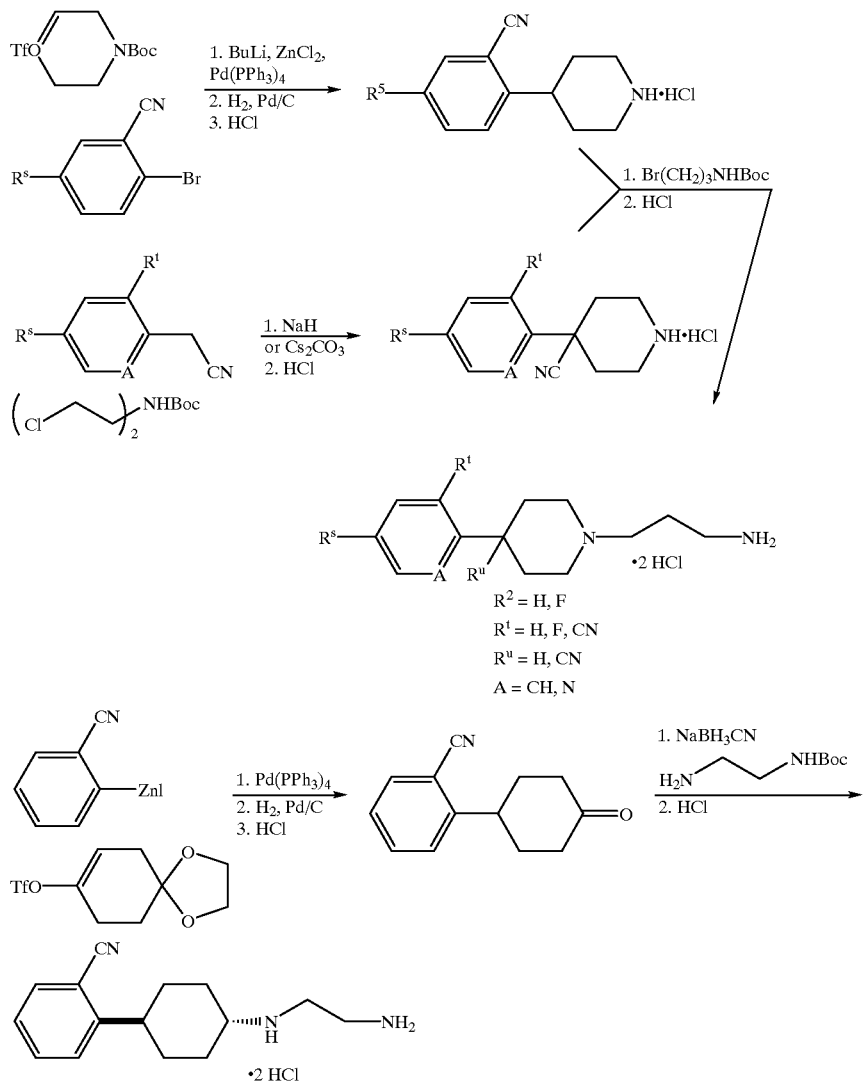

$R^2$ = H, F
$R^t$ = H, F, CN
$R^u$ = H, CN
A = CH, N

The following Examples further describe and illustrate the invention and its practice and are not to be construed as limiting the scope or spirit of the invention.

EXAMPLE 1

3-[4-(2-Pyridyl)-piperidin-1-yl]propylamine

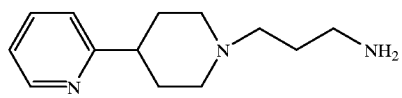

Step A. 1-(3-Aminopropyl)-4-[2-pyridyl]pyridinium bromide hydrobromide

A solution of 2,4'-dipyridyl (25 g, 160 mmol) and 3-bromopropylamine hydrobromide (35 g, 160 mmol) in DMF (60 mL) was heated at 90–95° C. for 10 h. After cooling to room temperature, anhydrous ether (500 mL) was added to the mixture. The resulting white solid was filtered, washed with ether and dried.

$^1$H NMR (300 MHz, DMSO) δ 2.35–2.44 (m, 2 H), 3.08–3.13 (m, 2 H), 4.76–4.81 (m, 2 H), 7.58 (dd, J=4.8 Hz, J=7.5 Hz, 1 H), 8.03 (dt, J=1.8 Hz, J=7.8 Hz, 1 H), 8.32 (d, J=7.8 Hz, 1 H), 8.77–8.81 (m, 3 H), 9.12 (d, J=6.3 Hz, 2 H). Anal. Calcd. for $C_{13}H_{16}N_3Br.HBr.0.5$ $H_2O$: C, 40.65; H, 4.72; N, 10.94. Found: C, 40.83; H, 4.37; N, 11.05.

Step B. 3-(3',6'-Dihydro-2'-H-[2,4']bipyridinyl-1'-yl)-propylamine

To a solution of 1-(3-aminopropyl)-4-[2-pyridyl] pyridinium bromide hydrobromide (6 g, 16 mmol) in MeOH (150 mL) at 0° C. was added $NaBH_4$ (2 g, 53 mmol) in small portions over a period of 2 h. The reaction mixture was stirred overnight at room temperature and the solvent was evaporated. The residue was suspended in ether (200 mL) and treated with 50% NaOH solution (100 mL). The ether layer was separated and the aqueous layer was extracted with ether (2×50 mL). The combined ether extracts were dried over potassium carbonate and the solvent was removed to give 3-(3',6'-dihydro-2'-H-[2,4']bipyridinyl-1'-yl)-propylamine as an oil. It was immediately used in the next step without purification.

Step C. 3-[4-(2-pyridyl)-piperidin-1-yl]propylamine

To a solution of 3-(3',6'-dihydro-2'-H-[2,4']bipyridinyl-1'-yl)-propylamine (3.48 g crude, 15.9 mmol) in MeOH (40 mL), was added 1.0 g of palladium hydroxide catalyst. The suspension was hydrogenated under 120 psi for 10 h after which the reaction mixture was filtered through a pad of Celite and the solvent was removed. The residue was purified by column chromatography over silica gel (30 g) [Note: If a large excess of silica gel is used the recovery of the product will be very low] using methylene chloridemethanol/2M ammonia in MeOH (90:8:4 to 90:40:40) as eluent. The product was obtained as a pale yellow oil.

$^1$H NMR δ (CD$_3$OD) 1.50–1.99 (m, 10 H), 2.02–2.06 (m, 2 H), 2.37–2.75 (m, 3 H), 3.02–3.06 (br m, 2 H), 7.05–7.09 (m, 4 H), 7.16 (dt, J=0.9Hz, J=8.7 Hz, 1 H), 8.48 (dd, J=0.9 Hz, J=4.2 Hz, 1 H).

EXAMPLE 2

3-[4-(4-Fluorophenyl)piperidin-1-yl]propylamine

Step A. 4-(4-Fluorophenyl)piperidine hydrochloride

To a solution of 4-(4-fluorophenyl)-1,2,3,6-tetrahydropyridine hydrochloride (10 g) in methanol (200 mL) was added 10% palladium on charcoal (0.5 g) and the mixture was hydrogenated at 50 psi for 3 h. The catalyst was removed by filtration and solvent was evaporated to leave the product as a white powder, which was used in the next step without any purification.

MP 181–182° C.

$^1$H NMR (CDCl$_3$): δ 1.95–2.03 (br d, 2H), 2.14–2.29 (m, 2H), 2.70–2.80 (m, 1H), 2.91–3.07 (br q, 2H), 3.60–3.64 (br d, 2H), 6.96–7.03 (m, 2H), 7.19–7.22 (m, 2H), 9.60 (br s, 1H), 9.71 (br s, 1H).

Step B. 3-[4-(4-Fluorophenyl)piperidin-1-yl] propylphthalimide

A mixture of 4-(4-fluorophenyl)piperidine hydrochloride (5.08 g, 23.2 mmol), 3-bromopropylphthalimide (6.22 g, 23.2 mmol), and potassium carbonate (15 g) in DMF (100 mL) was stirred and heated at 95–100° C. for 12 h. About 80% of the solvent was evaporated at reduced pressure, the residue was diluted with ethyl acetate (200 mL) and washed with brine (3×100 mL) and dried (Na$_2$SO$_4$). Solvent was evaporated and the residue was purified by column chromatography on silica gel using 1/1 hexane-ethyl acetate to 100% ethyl acetate as eluent. This product was crystallized from isopropanol to give a white crystalline solid; m.p. 80–81° C. This material was used in the next step. Concentration of the mother liquor and cooling gave the second crop.

$^1$H NMR (CDCl$_3$): δ 1.43–1.52 (m, 2H), 1.67–1.75 (m, 2H), 1.80–1.96 (m, 4H), 2.33–2.46 (m, 3H), 2.94–2.99 (br d, 2H), 3.78 (t, J=7 Hz, 2H), 6.90–7.04 (m, 4H), 7.70–7.74 (m, 2H), 7.84–7.87 (m, 2H).

Step C. 3-[4-(4-Fluorophenyl)piperidin-1-yl]propylamine

To a solution of 3-[4-(4-fluorophenyl)piperidin-1-yl] propylphthalimide (4.5 g, 12.3 mmol) in methanol (200 mL) was added 4 ml of hydrazine and the mixture was stirred and refluxed for 8 h. It was cooled, and the white solid was filtered and washed with methanol (20 mL). Solvent was evaporated, and the residue was dried under vacuum for 4 h. Chloroform (50 mL) was added to this material, it was stirred for 1 h and filtered. The white solid was washed with more chloroform (20 mL), and the solvent was evaporated from the combined filtrates to leave the crude product as an oil. It was purified by column chromatography on silica gel using dichloromethane/methanol/2M ammonia in methanol (10/3/1) as the eluent.

$^1$H NMR (CDCl$_3$): δ 1.60–1.83 (m, 6H), 1.96–2.07 (m, 4H), 2.40–2.55 (m, 3H), 2.70–2.85 (br t, 2H), 3.03–3.07 (br d, 2H), 6.93–7.00 (m, 2H), 7.14–7.20 (m, 2H).

EXAMPLE 3

3-[4-(2-Cyano-4-fluorophenyl)-piperidin-1-yl] propylamine, hydrochloride salt

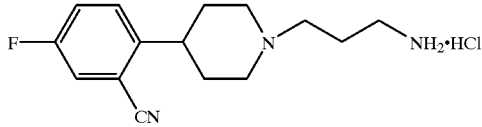

Step A. 4-(2–Cyano-4-fluorophenyl)-3,6-dihydro-2H-pyridine-1-carboxylic acid tert-butyl ester A solution of 2-bromo-5-fluorobenzonitrile (8.1 g, 40.5 mmole) in THF (50 mL) was added rapidly to a solution of n-BuLi (20 mL, 2.5M, 50 mmole) in THF at −78° C. and the resulting solution is stirred for 5 minutes. To this solution was added ZnCl$_2$, (0.5 M in THF, 89 mL, mmoles) and the solution was warmed to 0° C. Palladium tetrakistriphenylphosphine (1.5 g, 1.3 mmole) was added followed by trifluoromethanesulfonic acid [1-tert-butoxycarbonyl-(1,2,3,6-tetra-hydropyridin-4-yl)] ester from Example 7, step A below (9 g, 27.16 mmole). The reaction was heated to 40° C. for 30 minutes and then cooled to room temperature and poured into saturated aqueous sodium bicarbonate (1 L). The mixture was extracted with ethyl acetate (3×300 mL) and the combined organic extracts were dried over anhydrous magnesium sulfate, filtered and concentrated at reduced pressure. The residue was chromatographed on silica gel eluting with 15% to 30% ethyl acetate/hexanes to give the product.

$^1$H NMR (CDCl$_3$): δ 7.4–7.25 (m, 3H), 5.95 (br s, 1H), 4.09 (br s, 2H), 3.65–3.60 (m, 2H), 2.50 (m, 2H), 1.50 (s, 9H).

Step B. 4-(2-Cyano-4-fluorophenyl)-piperidine-1-carboxylic acid tert-butyl ester 4-(2-Cyano-4-fluorophenyl)-3,6-dihydro-2H-pyridine-1-carboxylic acid tert-butyl ester (7.89 g, 26.1 mmol) and 10% Palladium on carbon (3.95 g) were combined in absolute ethanol (270 ml) containing acetic acid (0.79 ml) and the mixture hydrogenated at 60 psi for 2.5 hrs. The catalyst was removed by filtration through super cel and the filtrate concentrated to dryness in vacuo to give a crude oil. Flash chromatography on silica gel (10% to 15% ethyl acetate in hexane) gave the product as a colorless oil.

$^1$H NMR (CDCl$_3$): δ 7.35–7.25 (m, 3H), 4.30–4.11 (br d, 2H), 3.15–3.06 (m, 1H), 2.91–2.82 (t, 2H), 1.87–1.82 (br d, 2H), 1.68–1.62 (m, 2H), 1.49 (s, 9H).

Step C. 4-(2-cyano-4-fluorophenyl) piperidine hydrochloride

An ethyl acetate solution (56 ml) of 4-(2-Cyano-4-fluorophenyl)-piperidine-1-carboxylic acid tert-butyl ester (5.64 g, 18.5mmol) was cooled to 0° C. and hydrogen chloride gas was bubbled through the solution until saturated (10 min). The solution was stirred in the cold (20 min) and then concentrated in vacuo to give the product as a white solid.

$^1$H NMR (CD$_3$OD): δ 7.61–7.53 (m, 2H), 7.53–7.43 (m, 1H), 3.60–3.50 (m, 2H), 3.40–3.16 (m, 3H), 2.18–1.94 (m, 4H).

Step D. 3-[4-(2-Cyano-4-fluorophenyl)-piperidin-1-yl]propylamine, hydrochloride

A suspension of 4-(2-cyano-4-fluorophenyl) piperidine hydrochloride (2.5 g, 10.4 mmol), 3-bromo-1-tert-butoxycarbonylpropylamine (3.22 g, 13.5 mmol) and triethylamine (3.76 ml, 27 mmol) in DMF (12 ml) was stirred at room temperature for 16 hours. The reaction mixture was diluted with ethyl acetate (200 mL)and washed with saturated bicarbonate solution, water×2 and brine. Drying and solvent evaporation gave after flash chromatography (silica gel, ethyl acetate) 3.1 g of 2-[1-(3-tert-butoxycarbonylaminopropyl) piperidin-4-yl]-4-fluorobenzonitrile. This material was dissolved in EtOAc (200 mL), cooled to 0° C. and HCl gas was bubbled into the solution for 15 minutes. The reaction mixture was concentrated at reduced pressure to give the the title compound.

$^1$H NMR (CD$_3$OD): δ 7.65–7.50 (m, 2H), 7.5–7.43 (m, 1H), 3.75–3.65 (m, 2H), 3.40–3.1 (m, 3H), 2.25–2.1 (m, 4H).

EXAMPLE 4

3-[4-(4-Fluorophenyl)-4-cyano-piperidin-1-yl]propylamine, dihydrochloride salt

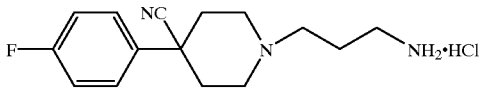

Step A. Bis-(2-chloro-ethyl)-tert-butoxycarbonylamine

To a solution of bis(2-chloroethyl)amine hydrochloride (10 g, 56.66 mmol) in 210 ml 2.5:1 dioxane:H$_2$O was added triethylamine (7.88 mL, 56.66 mmol). This solution was cooled to 0° C. under argon, and Boc anhydride (14.96, 68.58 mmol) was added dropwise. This was stirred for 45 min, poured onto saturated sodium bicarbonate, and extracted with ethyl acetate. The combined organic layers were washed with saturated sodium chloride, dried with magnesium sulfate, and concentrated in vacuo to give the product.

$^1$H NMR δ$_H$ (CDCl$_3$) 3.70–3.55 (m, 8H), 1.47 (s, 9H).

Step B. 4-(4-Fluorophenyl)-4-cyano-tert-butoxycarbonylpiperidine

To a solution of bis-(2-chloro-ethyl)-tert-butoxycarbonylamine (3.0 g, 12.39 mmol) in 75 mL of DMF was added 4-fluorobenzylacetonitrile (1.515 g, 11.27 mmol). This solution was cooled to 0° C., and a 60% dispersion of sodium hydride was added portion wise (1.17 g, 29.25 mmol). The solution was stirred for 20 min, warmed to room temperature, then heated to 80° C. for 24 h. It was poured onto water, and extracted with ethyl acetate. The combined organic layers were washed with saturated sodium chloride, dried with magnesium sulfate, and concentrated in vacuo. The crude material was passed through silica (25% ethyl acetate, hexane) to give the product.

$^1$H NMR δ$_H$ (CDCl$_3$) 7.50–7.40 (m, 2H), 7.15–7.05 (m, 2H), 4.40–4.20 (br m, 2H), 3.30–3.10 (br m, 2H), 2.15–2.05 (m, 2H), 2.00–1.85 (m, 2H), 1.49 (s, 9H).

Step C. 4-(4-Fluorophenyl)-4-cyano-piperidine hydrochloride

A solution of 4-(4-fluorophenyl)-4-cyano-tert-butoxycarbonylpiperidine (840 mg, 2.74 mmol) in 50 mL ethyl acetate was cooled to 0° C. Hydrogen chloride gas was bubbled through the solution for 2 min. It was stirred for 10 min and then concentrated in vacuo to give the product.

$^1$H NMR δ$_H$ (CD$_3$OD) 7.65–7.55 (M, 2H), 7.30–7.20 (m, 2H), 3.68–3.60 (m, 2H), 3.45–3.00 (m, 2H), 2.50–2.25 (m, 4H).

Step D. 1-(3-tert-Butoxycarbonylamino-propyl)-4-(4-fluorophenyl)-4-cyano-piperidine The free base of 4-(4-fluorophenyl)-4-cyano piperidine hydrochloride was prepared by pouring the salt onto saturated sodium carbonate extracting with ethyl acetate, drying the organic layers with sodium sulfate, filtering, and concentrating in vacuo. To a solution of 4-(4-fluorophenyl)-piperidine-4-carbonitrile (300 mg, 1.578 mmol) in 4 mL of DMF was added 3-bromopropyl-tert-butoxycarbonylamine (387 mg, 1.626 mmol) and triethylamine (225 mL, 1.623 mmol) under argon. The solution was stirred for 2 h at 60° C., poured onto saturated sodium bicarbonate, and extracted with ethyl acetate. The combined organic layers were washed with saturated sodium chloride, dried with magnesium sulfate, and concentrated in vacuo . The crude material was passed through silica (5% methanol, dichloromethane) to give the product.

$^1$H NMR δ$_H$ (CDCl$_3$) 7.50–7.45 (m, 2H), 7.15–7.05 (m, 2H), 5.40 (br s, 1H), 3.23–3.21 (m, 2H), 3.06–3.02 (m, 2H), 2.55–2.46 (m, 4H), 2.10–2.06 (m, 4H), 1.70–1.64 (m, 2H).

Step E. 3-[4-(4-Fluorophenyl)-4-cyano-piperidin-1-yl]propylamine, dihydrochloride salt A solution of 1-(3-tert-butoxycarbonylamino-propyl)-4-(4-fluorophenyl)-4-cyano piperidine (480 mg, 1.33 mmol) in 50 mL ethyl acetate was cooled to 0° C. Hydrogen chloride gas was bubbled through the solution for 2 min, and it was stirred for 20 min and then concentrated in vacuo to give the title product.

$^1$H NMR δ$_H$ (CD$_3$OD) 7.66–7.61 (m, 2H), 7.26–7.20 (m, 2H), 3.85–8.81 (m, 2H), 3.45–3.25 (m, 4H), 3.10 (t, 2H, J=7.6 Hz), 2.60–2.52 (m, 4H), 2.28–2.15 (m, 2H).

EXAMPLE 5

3-[4-(2-Cyano-4-fluorophenyl)-4-cyano-piperidin-1-yl]propylamine, hydrochloride salt

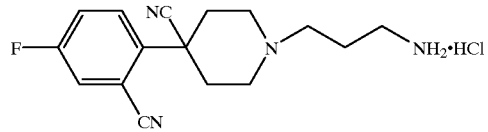

Step A. 2-Cyano-4-fluorophenylacetonitrile

A solution of 1.0 g (7.2 mmol) 2,5-difluorobenzonitrile, 1.2 ml (8.4 mmol) tert-butyl cyanoacetate, and 3.5 g (10.7 mmol) cesium carbonate in 30 ml DMSO was heated to 100° C. for 2 hours. The reaction was cooled to room temperature, diluted with 600 ml ether, washed with 300 ml 10% KHSO$_4$, 300 ml dilute brine, and 300 ml brine. The ether layer was dried over MgSO$_4$, filtered, and concentrated to give 1.6 g of an oil (TLC Rf=0.34 (20% EtOAc:hexanes)). This oil was dissolved in 100 ml 1,2-dichloroethane and 0.5 ml trifluoroacetic acid was slowly added. The reaction was heated to reflux for 4 hours, cooled, diluted with 200 ml ether, washed with 100 ml saturated aqueous sodium bicarbonate solution, 100 ml brine, then dried over MgSO4, filtered, and concentrated in vacuo. Purification by flash chromatography (4×12 cm silica gel, linear gradient 20–50% EtOAc:hexanes) afforded the title compound.

$^1$H NMR (300 MHz, CDCl$_3$) δ 7.64 (m, 1H); 7.41 (m, 2H); 3.95 (s, 2H).

Step B. 4-Cyano-4-(2-cyano-4-fluorophenyl)-piperidine-1-carboxylic acid tert butyl ester.

To a solution of 0.098 g (0.61 mmol) 2-cyano-4-fluorophenylacetonitrile and 0.17 g (0.07 mmol) N-Boc-di-(2-chloroethyl)amine in 3 ml DMSO was added 0.69 g (2.1 mmol) cesium carbonate. The reaction was stirred 24 h at room temperature, then diluted with 100 ml ethyl acetate, washed with 100 ml aqueous 10% KHSO$_4$ solution, 100 ml saturated sodium bicarbonate solution, 100 ml brine; then dried over Na$_2$SO$_4$, filtered and concentrated in vacuo. Purification by flash chromatography (3×12 cm silica gel, linear gradient 0–4% acetone/CH$_2$Cl$_2$) afforded the title compound. TLC Rf=0.25 (30% EtOAc:hexanes).

H NMR (400 MHz, CDCl$_3$) δ 7.65 (m, 1H); 7.50 (m, 1H); 7.37 (m, 1H); 4.37 (br m, 2H); 3.25 (br m, 2H); 2.30 (m, 4H); 1.50 (s, 9H).

Step C. 1-(3-N-Bocaminopropyl)-4-cyano-4-(2-cyano-4-fluorophenyl)-piperidine.

To a 0° C. solution of 0.53 g (1.63 mmol) 4-cyano-4-(2-cyano-4-fluorophenyl)-piperidine-1-carboxylic acid tert butyl ester in 10 ml ethyl acetate was bubbled through HCl gas for 5 minutes. The heterogeneous reaction mixture was stirred 5 more minutes at 0° C., then diluted with 70 ml EtOAc and extracted 2×75 ml H$_2$O. The combined aqueous extracts were brought to pH 11 with 3 ml 50% aqueous NaOH and extracted 3×50 ml ethyl acetate, adding solid NaCl to each extraction. The combined organic extracts were dried over Na$_2$SO$_4$, filtered and concentrated to give 0.33 g of an oil that was dissolved in 10 ml DMF. To this was added 0.3 ml (2.1 mmol) triethylamine and 0.38 g (1.6 mmol) N-Boc- 3-bromopropylamine. The reaction mixture was stirred 24 hours at room temperature, then diluted with 200 ml ethyl acetate, washed with 100 ml saturated aqueous sodium bicarbonate solution, 100 ml water, and 100 ml brine; then dried over Na$_2$SO$_4$, filtered and concentrated in vacuo. Purification by flash chromatography (3×12 cm silica gel, linear gradient 2–5% MeOH/1% NH$_4$OH/CH$_2$Cl$_2$) afforded the title compound.

$^1$H NMR (400 MHz, CDCl$_3$) δ 7.60 (dd, 1H, J=9.16 and 5.13 Hz); 7.51 (dd, 1H, J=7.69 and 2.93 Hz); 7.35 (m, 1H); 5.10 (br s, 1H); 3.20 (m, 2H); 3.08 (d, 2H, J=12.5 Hz); 2.54 (m, 4H); 2.40 (d, 2H, J=12.5 Hz); 2.25 (dt, 2H, J=2.54 and 11.9 Hz); 1.70 (quint, 2H, J=6.45 Hz); 1.43 (s, 9H).

Step D. 3-[4-(2-Cyano-4-fluorophenyl)-4-cyano-piperidin-1-yl]propylamine, dihydrochloride salt To a 0° C. solution of 0.38 g (1 mmol) mmol) 1-(3-N-Bocaminopropyl)-4-cyano-4-(2-cyano-4-fluorophenyl)-piperidine in 5 ml ethyl acetate was bubbled through HCl gas for 5 minutes. The heterogeneous reaction mixture was stirred 5 more minutes at 0° C., then concentrated in vacuo to give the title product.

$^1$H NMR (300 MHz, CD$_3$OD) δ 7.82 (dd, 1H, J=8.06 and 2.93 Hz); 7.75 (dd, 1H, J=8.79 and 4.88 Hz); 7.60 (m, 1H); 3.95 (d, 2H, J=13.0 Hz); 3.41 (m, 4H); 3.10 (t, 2H, J=7.57 Hz); 2.90 (m, 2H); 2.63 (br t, 2H, J=14.7 Hz); 2.23 (m, 2H).

EXAMPLE 6

3-[4-(2,4-difluorophenyl)-4-cyano-piperidin-1-yl]propylamine, dihydrochloride salt

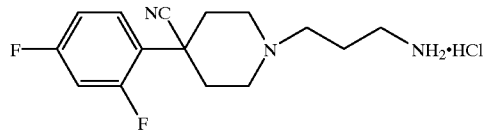

The title product was prepared by procedures similar those described above for Example 4 except substituting 2,4-difluorophenyl acetonitrile in Step B.

$^1$H NMR δ$_H$ (CD$_3$OD) 7.66–7.55 (m, 2H), 7.21–7.05 (m, 2H), 3.90–3.85 (m, 2H), 3.55–3.25 (m, 4H), 3.15–3.05 (m, 2H), 2.70–2.55 (m, 4H), 2.30–2.015 (m, 2H).

EXAMPLE 7

3-[4-(2-Cyanophenyl)-piperidin-1-yl]propylamine, hydrochloride salt

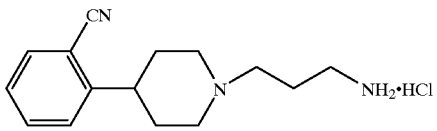

Step A. Trifluoromethanesulfonic acid[1-tert-butoxycarbonyl-(1,2,3,6-tetrahydro-pyridin-4-yl)]ester

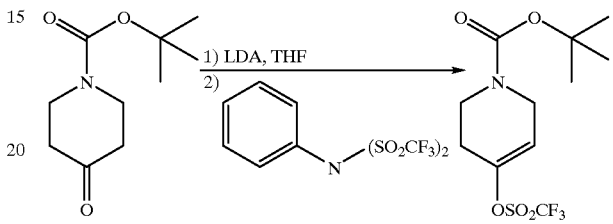

To a solution of diisopropylamine (13.4 ml, 0.096 mol) in tetrahydrofuran (400 ml), cooled to −78° C. was added n-butyllithium (2.5 M in hexanes, 38.4 ml, 0.096 mol) followed by addition of 1-tert-butoxycarbonyl-4-piperidone (16 g, 0.080 mol) in tetrahydrofuran (200 ml). After stirring for 10 minutes, a solution of N-phenyltrifluoromethane sulfonimide (31.4 g, 0.088 mol) in tetrahydrofuran (100 ml) was added. The reaction mixture was stirred for 15 minutes at −78° C., allowed to warm to room temperature and quenched with saturated bicarbonate solution. The reaction was diluted with ether and washed with 15% potassium hydrogen sulfate, saturated bicarbonate solution, 1N sodium hydroxide×4, water×2 and brine. Drying and solvent evaporation gave a solid; flash chromatography (silica gel, hexane-ethyl acetate, 95:5) gave trifluoromethanesulfonic acid[1-tert-butoxycarbonyl-(1,2,3,6-tetrahydropyridin-4-yl)]ester.

$^1$H NMR (CDCl$_3$) δ 1.48 (s, 9H), 2.44 (m, 2H), 3.63 (t, 2H, J=5.6 Hz), 4.04 (d, 2H, J=2.6 Hz), 5.76 (bs, 1H)

Step B. 2-[1-tertbutoxycarbonyl-(1,2,3,6-tetrahydropyridin-4-yl)]benzonitrile

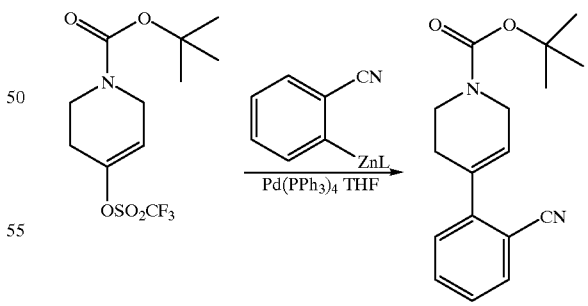

To a suspension of trifluoromethanesulfonic acid[1-tert-butoxycarbonyl-(1,2,3,6-tetrahydropyridin-4-yl)]ester (10.5 g, 0.032 mol) and tetrakis(triphenylphosphine) palladium(0) (1.8 g, 1.6 mmol) in tetrahydrofuran (95 ml) was added iodo(2-cyanophenyl)zinc (0.5M in tetrahydrofuran, 94 ml, 0.047 mol) dropwise. The reaction mixture was stirred at room temperature for 0.5 hours and quenched with saturated bicarbonate solution. The mixture was diluted with ethyl acetate and washed with water×2 and brine. Drying and solvent evaporation gave an oil; flash chromatography (silica gel, hexane-ethyl acetate, 92:8) gave the title compound.

$^1$H NMR (CDCl$_3$) δ 1.50 (s, 9H), 2.53 (m, 2H), 3.67 (t, 2H, J=6.0 Hz), 4.12 (d, 2H, J=3.2 Hz), 5.98 (m, 1H), 7.34 (m, 2H), 7.54 (bt, 1H, J=7.6 Hz), 7.66 (bd, 1H, J=8 Hz).

Step C. 2-(1-tert-Butoxycarbonylpiperidin-4-yl)benzonitrile

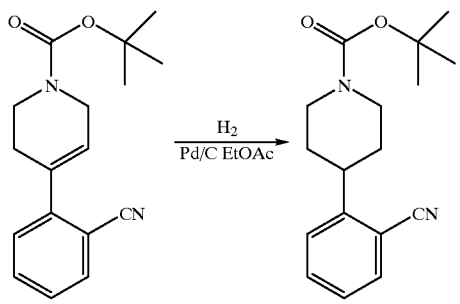

To a solution of 2-[(1-tert-butoxycarbonyl-(1,2,3,6-tetrahydropyridin-4-yl)]benzonitrile (5.3 g, 0.019 mol) and acetic acid (0.28 ml, 4.9 mmol) in ethanol (200 ml), degassed with argon was added palladium on carbon. The reaction was hydrogenated on a Parr apparatus at 50 psi for 15 hours. The mixture was recharged twice with acetic acid (0.14 ml, 0.28 ml) and palladium on carbon (900 mg, 1.8 g), hydrogenated as above and filtered through celite. Solvent evaporation gave 2-(1-tert-butoxycarbonylpiperidin-4-yl) benzonitrile.

$^1$H NMR (CDCl$_3$) δ 1.49 (s, 9H), 1.64 (m, 2H), 1.86 (bd, 2H, J=13.4 Hz), 2.88 (bt, 2H, J=14 Hz), 3.14 (tt, 1H, J=12 Hz, J=4 Hz), 4.27 (bs, 2H), 7.31 (m, 2H), 7.56 (bt, 1H, J=7.7 Hz), 7.63 (bd, 1H, J=7.7 Hz)

Step D. 2-(Piperidin-4-yl)benzonitrile hydrochloride

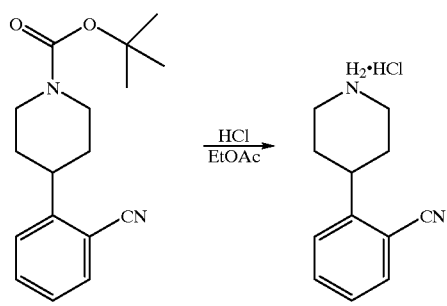

To a solution of 2-(1-tertbutoxycarbonylpiperidin-4-yl) benzonitrile (1.7 g, 5.9 mmol) in ethyl acetate (~50 ml), cooled to 0° C. was added hydrogen chloride gas, bubbled vigorously for 5 minutes. The reaction mixture was stirred for 10 minutes at 0° C., purged with argon and concentrated. Flushing with ethyl acetate×3 and concentration gave 2-(piperidin-4-yl) benzonitrile hydrochloride.

$^1$H NMR (DMSO) δ 1.98 (m, 4H), 3.07 (m, 2H), 3.21 (tt, 1H, J=12 Hz, J=3.8 Hz), 3.36 (m, 2H), 7.46 (m, 2H), 7.74 (bt, 1H, J=7.7 Hz), 7.83 (bd, 1H, J=7.0 Hz), 9.10 (bd, 2H).

Step E. 3-Bromo-1-tertbutoxycarbonylpropylamine

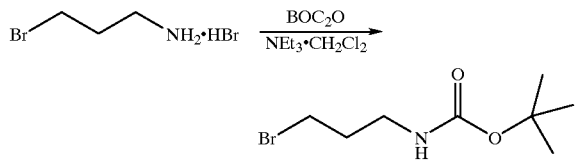

To a suspension of 3-bromopropylamine hydrobromide (5.0 g, 0.023 mol) and di-tert-butyl dicarbonate(5.0 g, 0.023 mol) in methylene chloride (125 ml), cooled to 0° C. was added triethylamine (3.2 ml, 0.023 mol). The reaction mixture was stirred for 3 hours at room temperature, diluted with methylene chloride and washed with water×2 and brine. Drying and solvent evaporation gave 3-bromo-1-tert-butoxycarbonylpropylamine.

$^1$H NMR (CDCl$_3$) δ 1.46 (s, 9H), 2.05 (m, 2H), 3.28 (m, 2H), 3.43 (m, 2H), 4.64 (bs, 1H).

Step F. 2-[1-(3-tert-Butoxycarbonylaminopropyl) piperidin-4-yl]benzonitrile

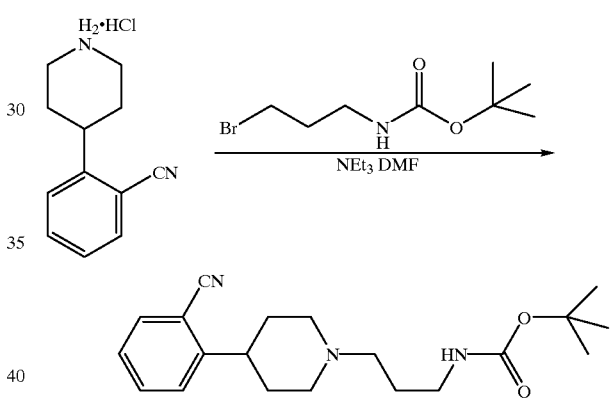

A suspension of 2-(piperidin-4-yl)benzonitrile hydrochloride (600 mg, 2.7 mmol), 3-bromo-1-tert-butoxycarbonylpropylamine (0.67 g, 2.8 mmol) and triethylamine (0.77 ml, 5.5 mmol) in DMF (12 ml) was stirred at room temperature for 15 hours. The reaction mixture was diluted with ethyl acetate and washed with saturated bicarbonate solution, water×2 and brine. Drying and solvent evaporation gave an oil (0.86 g); flash chromatography (silica gel, ethyl acetate) gave 2-[1-(3-tert-butoxycarbonylaminopropyl) piperidin-4-yl]benzonitrile.

$^1$H NMR (CDCl$_3$) δ 1.45 (s, 9H), 1.69 (m, 2H), 1.80 (bt, 2H, J=12 Hz), 1.89 (m, 2H), 2.12 (bt, 2H, J=10.8 Hz), 2.47 (t, 2H, J=6.7 Hz), 2.97–3.08 (m, 3H), 3.22 (m, 2H), 5.61 (bs, 1H), 7.29 (m, 1H), 7.39 (bd, 1H, J=7.9 Hz), 7.54 (bt, 1H, J=7.7 Hz), 7.62 (bd, 1H, J=7.7 Hz).

Step G. 3-[4-(2-Cyanophenyl)-piperidin-1-yl]propylamine, hydrochloride salt

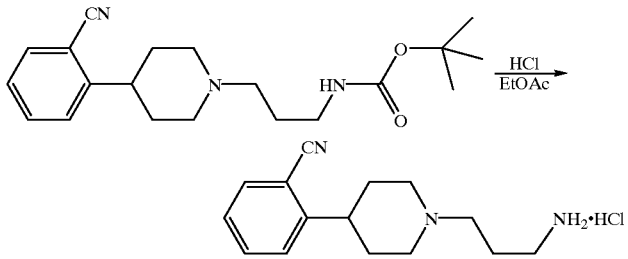

To a solution of 2-[1-(3-tert-butoxycarbonylamino-propyl)piperidin-4-yl]benzonitrile (0.73 g, 2.1 mmol) in ethyl acetate (100 ml), cooled to 0° C. was added hydrogen chloride gas, bubbled vigorously for 5 minutes. The reaction mixture was stirred for 10 minutes at 0° C., purged with argon and concentrated. Flushing with ethyl acetate×2 and concentration gave the title product.

$^1$H NMR (DMSO) δ 2.00 (m, 2H), 2.10 (m, 2H), 2.28 (m, 2H), 2.95 (m, 2H), 3.18 (m, 4H), 3.56 (bd, 2H, J=1.7 Hz), 7.47 (m, 2H), 7.75 (bt, 1H, J=8 Hz), 7.84 (bd, 1H, J=7.9 Hz), 8.14 (bs, 2H), 11.1 (bd, 1H).

EXAMPLE 8

3-[4-(2-Cyanophenyl)-4-cyano-piperidin-1-yl] propylamine, hydrochloride salt

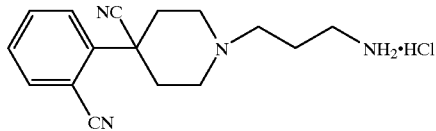

This product was prepared by a procedure similar to Example 5 starting with 2-fluorobenzonitrile.

$^1$H NMR $δ_H$ (CDCl$_3$) 7.97–7.95 (d, 1H, J=7.1 Hz), 7.83–7.80 (t, 1H, J=7.1), 7.72–7.63 (m, 2H), 3.95–3.90 (d, 2H, J=15 Hz), 3.51–3.29 (m, 4H), 3.12–3.07 (t, 2H, J=7.8), 2.93–2.88 (br m, 2H), 2.67–2.55 (m, 2H), 2.22–2.01 (m, 2H).

EXAMPLE 9 trans-2-[4-(2-Amino-ethylamino)-cyclohexyl]-benzonitrile hydrochloride cis-2-[4-(2-Amino-ethylamino)-cyclohexyl]-benzonitrile hydrochloride

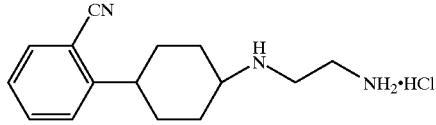

Step A. Trifluoromethanesulfonic acid 1,4-dioxa-spiro[4.5]dec-7-en-8-yl ester

To a solution of diisopropylamine (7.6 mL, 54.3 mmol) in 200 mL THF cooled to −78° C. was added n-butyllithium (21.8 mL 2.5 M in hexane, 54.3 mmol) under argon. The solution was stirred for 10 minutes, then a solution of 1,4-cyclohexanedione monoethylene ketal (8.5 g, 54.3 mmol) in 75 mL THF was added slowly. The solution was stirred for 10 min, then a solution of N-phenyltrifluoromethane sulfonamide (19.5 g, 54.3 mmol) in 150 mL THF was added slowly. The reaction solution was warmed to r.t., poured onto saturated sodium bicarbonate, and extracted with ethyl acetate. The combined organic layers were washed with saturated sodium chloride, dried with magnesium sulfate, and concentrated in vaccuo. The crude material was passed through silica (3% methanol, dichloromethane) to give the product as an oil.

$^1$H NMR $δ_H$ (CDCl$_3$) 5.7–5.6 (m, 1H), 4.1–4.0 (m, 4H), 2.6–2.5 (m, 2H), 2.5–2.4 (m, 2H), 1.9 (t, 2H, J 6.6).

Step B. 2-(1,4-Dioxaspiro[4.5]dec-7-en-8-yl)benzonitrile

To a solution of trifluoromethanesulfonic acid 1,4-dioxa-spiro[4.5]dec-7-en-8-yl ester (12.5 g, 45.2 mmol) in THF (100 mL) at room temperature was added a solution of iodozinc benzonitrile (100 mL of a 0.5 N solution in THF, 50 mmol) and palladium tetrakistriphenylphophine (1 g, 0.8 mmol). The reaction was heated to 80° C. for 1 hour. The reaction was cooled to room temperature and poured into saturated sodium bicarbonate (1L), and extracted with ethyl acetate. The combined organic layers were washed with saturated sodium chloride, dried with magnesium sulfate, and concentrated in vacuo. The crude material was chromatographed over silica gel eluting with 25% ethylacetate/hexane to give the product as a pale yellow oil.

$^1$H NMR $δ_H$ (CDCl$_3$) 7.7–7.6 (m, 1H), 7.52 (dt, 1H, J=2, 7 Hz), 7.4–7.26 (m, 2H), 5.95–5.88 (m, 1H), 4.05–4.0 (m, 4H), 2.7–2.6 (m, 2H), 2.55–2.48 (m, 2H), 1.95 (t, 2H, J=6.6 Hz).

Step C. 2-(1,4-Dioxaspiro[4.5]dec-8-yl)benzonitrile

To a suspension of 10% palladium on carbon (1.5 g) in ethyl acetate (200 mL) at room temperature under argon was added a solutioin of 2-(1,4-dioxaspiro[4.5]dec-7-en-8-yl) benzonitrile (8.9 g, 36.7 mmol) in ethyl acetate (50 mL). Hydrogen gas was then bubbled into the reaction mixture until all the starting material was consumed. The reaction was filtered through celite to remove the catalyst and the solution concentrated to give the product as a colorless oil.

$^1$H NMR $δ_H$ (CDCl$_3$) 7.65–7.6 (m, 1H), 7.54 (dt, 1H, J=2, 7 Hz),7.46 (br d, 2H, J=7 Hz), 7.28 (dt, 1H, J=2, 7 Hz), 4.05–4.0 (m, 4H), 3.1–3.0 (m, 1H), 2.0–1.7 (m, 8H)

Step D. 2-(4-Oxocyclohexyl)benzonitrile

To a stirring solution of 2-(1,4-dioxaspiro[4.5]dec-8-yl) benzonitrile (8.7 g, 35.7 mmol) in dioxane (200 mL) was added 1N HCl (200 mL) and the reaction heated to 80° C. for 2 hours. The reaction was cooled to room temperature and poured into water (1 L) the mixture was extracted with ethyl acetate (3×250 mL). The combined organics were washed with brine (200 mL) and then dried over anhydrous magnesium sulfate, filtered and concentrated at reduced pressure to give the product.

$^1$H NMR $δ_H$ (CDCl$_3$) 7.65–7.6 (br d, 1H, J=7 Hz), 7.59 (br t, 1H, J=7 Hz),7.40–7.30 (m, 2H), 3.5 (tt, 1H, J=3, 10 Hz), 2.7–2.5 (m, 4H), 2.35–2.2 (m, 2H), 2.05–1.90 (m, 2H).

Step E. trans-2-[4-(2-Amino-ethylamino)-cyclohexyl]-benzonitrile hydrochloride and cis-2-[4-(2-Amino-ethylamino)-cyclohexyl]-benzonitrile hydrochloride To a solution of 2-(4-oxocyclohexyl)benzonitrile (2.0 g, 10.0 mmol) and acetic acid (2.15 mL, 15.0 mmol) in 50 mL methanol was addded N-tert-butoxycarbonyl-ethylenediamine (2.40 g, 15.0 mmol) under argon. The solution was stirred for 2 h, then sodium cyanoborohydride (14.8 mL 1M in THF, 15.0 mmol) was added dropwise. The solution was poured onto saturated sodium bicarbonate, and extracted with ethylacetate. The combined organic layers were washed with saturated sodium chloride, dried with magnesium sulfate, and concentrated in vaccuo. The crude material was passed through silica (10% methanol, ethylactate) to give 3:1 trans:cis 2-[4-(2-tertbutoxycarbonylamino-ethylamino)-cyclohexyl]-benzonitrile.

The trans-2-[4-(2-tertbutoxycarbonylamino-ethylamino)-cyclohexyl]-benzonitrile was dissolved in 200 mL ethylacetate, and HCl gas was bubbled through the solution for 1 h. The solution was concentrated in vaccuo to give the trans product.

$^1$H NMR $\delta_H$ (CD$_3$OD) 7.75–7.60 (m, 2H), 7.52–7.49 (d, 1H, J=7.8 Hz), 7.42–7.39 (t, 1H, J=7.6 Hz), 3.38–3.36 (m, 4H), 3.07–3.03 (m, 1H), 2.40–2.30 (m, 2H), 2.10–2.05 (m, 2H), 1.78–1.64 (m, 4H).

The cis-2-[4-(2-tertbutoxycarbonylamino-ethylamino)-cyclohexyl]-benzonitrile (0.343 g, 1.57 mmol) was dissolved in 200 mL ethyl acetate, and HCl gas was bubbled through the solution for 1 h. The solution was concentrated in vaccuo to give the cis product.

$^1$H NMR $\delta_H$ (CD$_3$OD) 7.82–7.80 (d, 1H, J-8.06 Hz), 7.79–7.63 (m, 2H), 7.41–7.35 (t, 1H, J=7.3 Hz), 3.60–3.50 (br s, 1H), 3.45–3.40 (m, 3H), 3.20–3.05 (m, 1H), 2.25–2.15 (m, 2H), 2.10–1.95 (m, 4H), 1.9–1.3 (m, 2H).

EXAMPLE 10

4-(R,S)-(3,4-Difluorophenyl)-6-methyl-3,4-dihydro-2-pyridinone-5-carboxylic acid

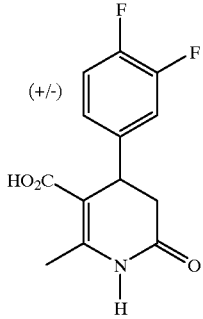

Benzyl acetoacetate (7.69 g, 40 mmol), dimethyl dioxane dione (Meldrum's acid, 5.77 g, 40 mmol), 3,4-difluorobenzaldehyde (5.68 g, 40 mmol) and ammonium acetate (3.24 g, 42 mmol) were combined in acetic acid (40 ml) and the reaction mixture was refluxed for 2.5 hrs. After cooling to room temperature the reaction mixture was poured on ice and the resulting mixture was diluted with water, extracted with diethyl ether and ethyl acetate. The organic layer was washed with brine, dried over MgSO$_4$, and concentrated in vacuo. The crude material was purified by flash chromatography (silica gel, 30% ethyl acetate in hexane to 50% and then silica gel, 50% diethyl ether in hexane to 100% diethyl ether) to provide after recrystalization from ethyl acetate/hexane: 4-(R,S)-(3,4-difluorophenyl)-6-methyl-3,4-dihydro-2-pyridinone-5-benzyl acetate as a white crystalline solid. A second crop was obtained from the mother liquor.

$^1$H NMR (CDCl$_3$): δ 8.35 (br s, 1H), 7.40–6.80 (m, 8H), 5.10 (AB q, 2H), 4.25 (d, 1H, X of ABX), 2.95 (dd, 1H, A of ABX), 2.65 (d, 1H, B of ABX), 2.45 (s, 3H).

A solution of 4-(R,S)-(3,4-difluorophenyl)-6-methyl-3,4-dihydro-2-pyridinone-5-benzyl acetate (1 g, 2.80 mmol) in ethanol (50 ml) and ethyl acetate (25 ml) was hydrogenated over 10% Pd/C (300 mg) for 2 hrs. After filtration on celite and concentration in vacuo, 4-(R,S)-(3,4-difluorophenyl)-6-methyl-3,4-dihydro-2-pyridinone-5-carboxylic acid (790 mg, >100%%) was obtained as a white solid.

$^1$H NMR (d$_6$ DMSO): δ 9.90 (s, 1H), 7.35 (m, 1H), 7.20 (m, 1H), 6.95 (m, 1H), 4.15 (d, 1H, X of ABX), 2.85 (dd, 1H, A of ABX), 2.40 (d, 1H, B of ABX), 2.30 (s, 3H).

EXAMPLE 11

4-(R,S)-(3,4-Difluorophenyl)-1,6-dimethyl-3,4-dihydro-2-pyridinone-5-carboxylic acid

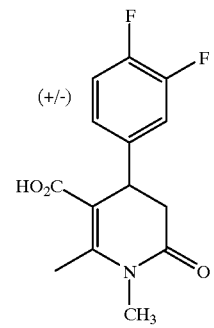

To a solution of 4-(R,S)-(3,4-difluorophenyl)-6-methyl-3,4-dihydro-2-pyridinone-5-benzyl acetate (2 g, 5.6 mmol) in DMF (10 ml) was added dimethyl sulfate (0.64 ml, 6.72 mmol) followed by sodium hydride (60% dispersion in oil, 246 mg, 6.16 mmol) by portions. After stirring at room temperature for 15 min, the reaction mixture was carefully quenched with water, diluted with 1N HCl, diethyl ether and ethyl acetate. The organic layer was extracted, washed with saturated aqueous sodium bicarbonate and brine, dried over MgSO$_4$, and concentrated in vacuo. The crude material was purified by flash chromatography (silica gel, 25% ethyl acetate in hexane to 35%) to provide 4-(R,S)-(3,4-difluorophenyl)-1,6-dimethyl-3,4-dihydro-2-pyridinone-5-benzyl acetate (2.03 g, 98%) which was hydrogenated following a similar procedure as described in example 5, to provide: 4-(R,S)-(3,4-difluorophenyl)-1,6-dimethyl-3,4-dihydro-2-pyridinone-5-carboxylic acid as a white solid.

$^1$H NMR (CDCl$_3$): δ 7.10 (m, 1H), 6.96–6.80 (m, 2H), 4.20 (d, 1H, X of ABX), 3.25 (s, 3H), 2.95 (dd, 1H, A of ABX), 2.80 (d, 1H, B of ABX), 2.60 (s, 3H).

EXAMPLE 12

(−)-4-(R)-(3,4-Difluorophenyl)-6-methyl-3,4-dihydro-2-pyridinone-5-carboxylic acid

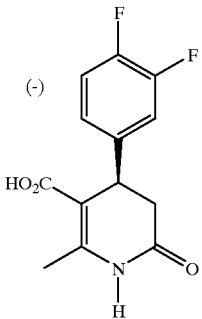

4-(R,S)-(3,4-difluorophenyl)-6-methyl-3,4-dihydro-2-pyridinone-5-benzyl acetate (example I) was resolved on Chiralcel OD (90:10:0.1 hexane:ethanol:diethyl amine) to provide the (+) enantiomer (1st fraction, $[a]_D$=+68.4° (c=0.53, MeOH) and provide the (−) enantiomer (2nd fraction, $[a]_D$=−67.4° (c=0.39, MeOH). Both enantiomers were hydrogenated as described in example I, providing (−)-4-(R)-(3,4-difluorophenyl)-6-methyl-3,4-dihydro-2-pyridinone-5-carboxylic acid ($[a]_D$=−80.4° (c=0.36, MeOH)) and its (+) enantiomer. The (+) enantiomer was converted to the less active (+) alpha-1 antagonist described in example 18 (the S enantiomer) thus identifying (−)-4-(R)-(3,4-difluorophenyl)-6-methyl-3,4-dihydro-2-pyridinone-5-carboxylic acid as the enantiomer leading to the more "active" alpha 1a antagonist by default.

EXAMPLE 13

(+)-4-(R)-(3,4-Difluorophenyl)-1,6-dimethyl-3,4-dihydro-2-pyridinone-5-carboxylic acid

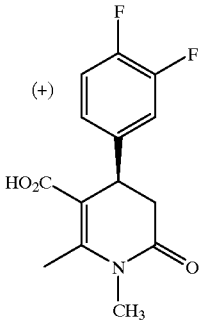

(−)-4-(R)-(3,4-difluorophenyl)-6-methyl-3,4-dihydro-2-pyridinone-5-benzyl acetate (Example 12) was methylated and hydrogenated using a similar procedure as described in Example 11 to provide (+)-4-(R)-(3,4-difluorophenyl)-1,6-dimethyl-3,4-dihydro-2-pyridinone-5-carboxylic acid:

$[a]_D$=+25.3° (c=0.40, MeOH).

EXAMPLES 14–33

The general procedure employed to prepare each of the compounds set forth in Examples 14–33 below was one of the following:

General Procedure A

To a solution of (−)-4-(R)-(3,4-difluorophenyl)-6-methyl-3,4-dihydro-2-pyridinone-5-carboxylic acid (see Example 12) or (+)-4-(R)-(3,4-difluorophenyl)-1,6-dimethyl-3,4-dihydro-2-pyridinone-5-carboxylic acid (see Example 13) (0.06 mmol) in DMF (0.1 ml) the following were added sequentially: triethyl amine (0.04 ml, 0.3 mmol), the primary amine of interest, mono or dihydrochloride.(0.06 mmol), 1-hydroxy-7-azabenzotriazole (8.2 mg, 0.06 mmol, in 0.25 ml DMF), and 1-ethyl-3-(3-dimethylaminopropyl)-carbodiimide hydrochloride 11.5 mg, 0.06 mmol, in 0.45 ml DMF). The reaction mixture was stirred by vortex for a few seconds and allowed to stand at room temperature for 16 hours. The crude mixture was purified by preparative reverse phase HPLC (C8, ACN, water, TFA). The products of interest were isolated as TFA salts after fraction selection and solvent evaporation. $^1$H NMR, MS, and analytical HPLC were used to assess identity and purity.

General Procedure B

To a solution of 4-(R,S)-(3,4-difluorophenyl)-6-methyl-3,4-dihydro-2-pyridinone-5-carboxylic acid (see Example 10) or 4-(R,S)-(3,4-difluorophenyl)-1,6-dimethyl-3,4-dihydro-2-pyridinone-5-carboxylic acid (see Example 11) (0.5 mmol, 1 eq) in DMF (20 ml) the following were added sequentially: triethyl amine (4 eq), the primary amine of interest, mono or dihydrochloride.(0.8 eq), 1-hydroxy-7-azabenzotriazole (1 eq), and 1-ethyl-3-(3-dimethylaminopropyl)-carbodiimide hydrochloride (1 eq). The reaction mixture was stirred at room temperature for 16 hours, diluted with ethyl acetate, washed with water, saturated aqueous sodium bicarbonate, water, and aqueous lithium chloride, dried over $Na_2SO_4$, and concentrated in vacuo. The crude material was purified by flash chromatography (silica gel, 2% (10% $NH_4OH$/MeOH) in methylene chloride to 4%) to provide the corresponding amide, racemic, as a free base or as the hydrochloride after treatment with 1 N HCl in diethyl ether.

The racemic material was resolved by preparative HPLC (Chiralpak AD or Chiralcel OJ) to provide both enantiomers as free bases or as the hydrochlorides after treatment with 1 N HCl in diethyl ether.

EXAMPLE 14

4-(R)-(3,4-Difluorophenyl)-6-methyl-3,4-dihydro-2-pyridinone-5-carboxylic acid{3-[4-(2-pyridyl)-piperidine-1-yl]-propyl}amide

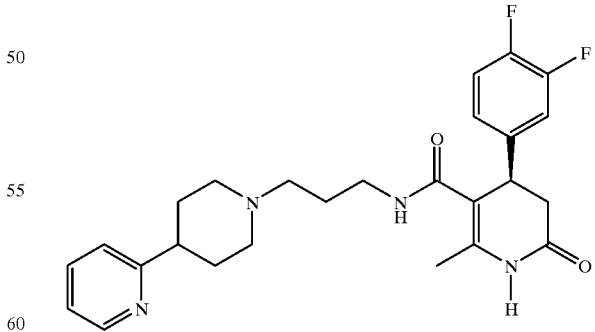

The title compound was prepared from 3-[4-(2-pyridyl)-piperidin-1-yl]propylamine (see Example 1) and (−)-4-(R)-(3,4-difluorophenyl)-6-methyl-3,4-dihydro-2-pyridinone-5-carboxylic acid in accordance with General Procedure A.

MS: M+H=469.25.

EXAMPLE 15

4-(R)-(3,4-Difluorophenyl)-1,6-dimethyl-3,4-dihydro-2-pyridinone-5-carboxylic acid{3-[4-(2-pyridyl)-piperidine-1-yl]-propyl}amide

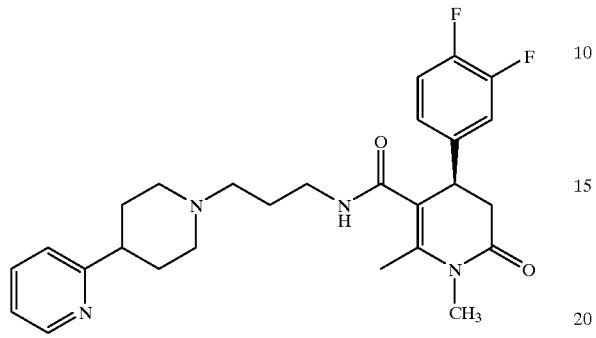

The title compound was prepared from 3-[4-(2-pyridyl)-piperidin-1-yl]propylamine (see Example 1) and (+)-4-(R)-(3,4-difluorophenyl)-1,6-dimethyl-3,4-dihydro-2-pyridinone-5-carboxylic acid in accordance with General Procedure A.

MS: M+H=483.26.

EXAMPLE 16

4-(R)-(3,4-Difluorophenyl)-6-methyl-3,4-dihydro-2-pyridinone-5-carboxylic acid{3-[4-(2-pyridyl)-4-cyano-piperidine-1-yl]-propyl}amide

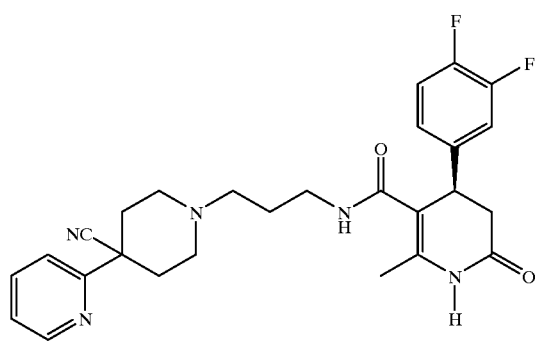

The title compound was prepared from 3-[4-(2-pyridyl)-4-cyano-piperidin-1-yl]propylamine (prepared using a procedure similar to that described in Example 4 above) and (−)-4-(R)-(3,4-difluorophenyl)-6-methyl-3,4-dihydro-2-pyridinone-5-carboxylic acid in accordance with General Procedure A.

MS: M+H=494.24.

EXAMPLE 17

4-(R)-(3,4-Difluorophenyl)-1,6-dimethyl-3,4-dihydro-2-pyridinone-5-carboxylic acid{3-[4-(2-pyridyl)-4-cyano-piperidine-1-yl]-propyl}amide

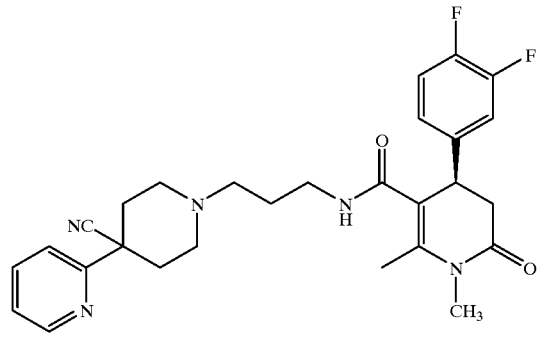

The title compound was prepared from 3-[4-(2-pyridyl)-4-cyano-piperidin-1-yl]propylamine (prepared using a procedure similar to that described in Example 4 above) and (+)-4-(R)-(3,4-difluorophenyl)-1,6-dimethyl-3,4-dihydro-2-pyridinone-5-carboxylic acid in accordance with General Procedure A.

MS: M+H=508.26.

EXAMPLE 18

4-(R)-(3,4-Difluorophenyl)-6-methyl-3,4-dihydro-2-pyridinone-5-carboxylic acid{3-[4-(4-fluorophenyl)-piperidine-1-yl]-propyl}amide The title compound was prepared from 3-[4-(4-fluorophenyl)-piperidin-1-yl]propylamine (see Example 2) and 4-(R,S)-(3,4-difluorophenyl)-6-methyl-3,4-dihydro-2-pyridinone-5-carboxylic acid in accordance with General Procedure B. $[\alpha]_D = -60.8°$ (c=0.24, MeOH).

The (S) enantiomer was also resolved from the racemate in the same procedure. $[\alpha]_D = +65.5°$ (c=0.2, MeOH).

EXAMPLE 19

4-(R)-(3,4-Difluorophenyl)-1,6-dimethyl-3,4-dihydro-2-pyridinone-5-carboxylic acid{3-[4-(4-fluorophenyl)-piperidine-1-yl]-propyl}amide

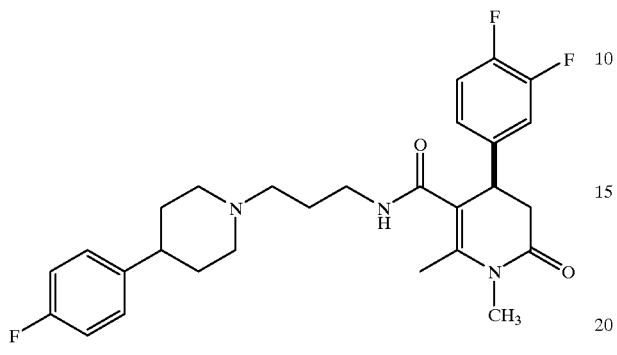

The title compound was prepared from 3-[4-(4-fluorophenyl)-piperidin-1-yl]propylamine (see Example 7) and 4-(R,S)-(3,4-difluorophenyl)- 1,6-dimethyl-3,4-dihydro-2-pyridinone-5-carboxylic acid in accordance with General Procedure B. $[\alpha]_D=+10°$ (c=0.2, MeOH).

The (S) enantiomer was also resolved from the racemate in the same procedure. $[\alpha]_D=-9.8°$ (c=0.18, MeOH).

EXAMPLE 20

4-(R)-(3,4-Difluorophenyl)-6-methyl-3,4-dihydro-2-pyridinone-5-carboxylic acid{3-[4-(2-cyano-4-fluorophenyl)-piperidine-1-yl]-propyl}amide

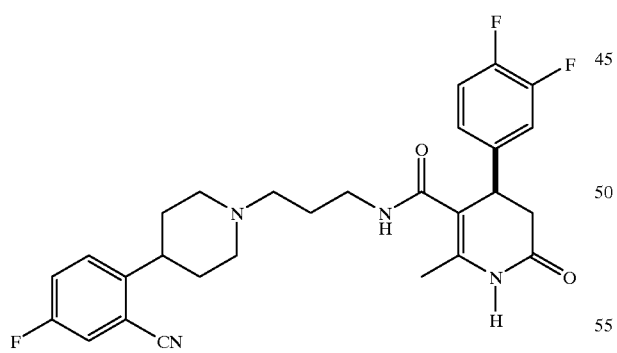

The title compound was prepared from 3-[4-(2-cyano-4-fluorophenyl)-piperidin-1-yl]propylamine (see Example 3) and (−)-4-(R)-(3,4-difluorophenyl)-6-methyl-3,4-dihydro-2-pyridinone-5-carboxylic acid in accordance with General Procedure A.

MS: M+H=511.23.

EXAMPLE 21

4-(R)-(3,4-Difluorophenyl)-1,6-dimethyl-3,4-dihydro-2-pyridinone-5-carboxylic acid{3-[4-(2-cyano-4-fluorophenyl)-piperidine-1-yl]-propyl}amide

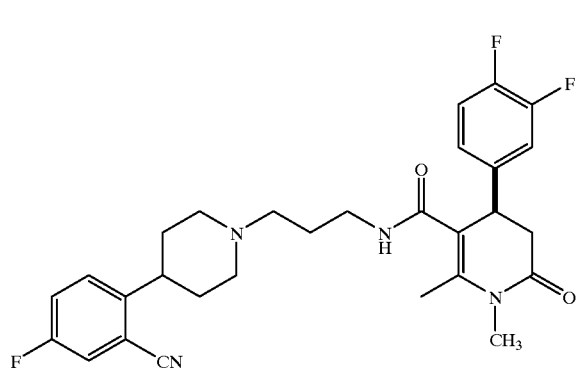

The title compound was prepared from 3-[4-(2-cyano-4-fluorophenyl)-piperidin-1-yl]propylamine (see Example 3) and (+)-4-(R)-(3,4-difluorophenyl)-1,6-dimethyl-3,4-dihydro-2-pyridinone-5-carboxylic acid in accordance with General Procedure A.

MS: M+H 525.25.

EXAMPLE 22

4-(R)-(3,4-Difluorophenyl)-6-methyl-3,4-dihydro-2-pyridinone-5-carboxylic acid{3-[4-(4-fluorophenyl)-4-cyano-piperidine-1-yl]-propyl}amide

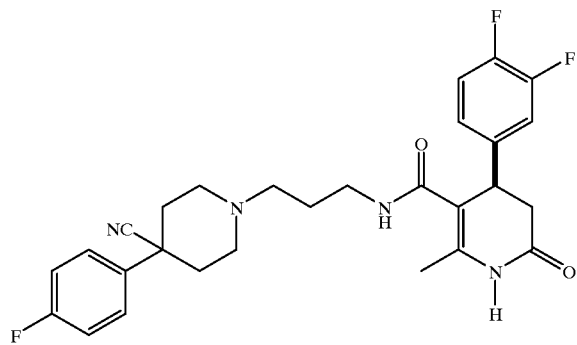

The title compound was prepared from 3-[4-(4-fluorophenyl)-4-cyano-piperidin-1-yl]propylamine (see Example 4) and 4-(R,S)-(3,4-difluorophenyl)-6-methyl-3,4-dihydro-2-pyridinone-5-carboxylic acid in accordance with General Procedure B. $[\alpha]_D=-55.6°$ (c=0.18, MeOH).

The (S) enantiomer was also resolved from the racemate in the same procedure. $[\alpha]_D=+54.3°$ (c=0.18, MeOH).

EXAMPLE 23

4-(R)-(3,4-Difluorophenyl)-1,6-dimethyl-3,4-dihydro-2-pyridinone-5-carboxylic acid{3-[4-(4-fluorophenyl)-4-cyano-piperidine-1-yl]-propyl}amide

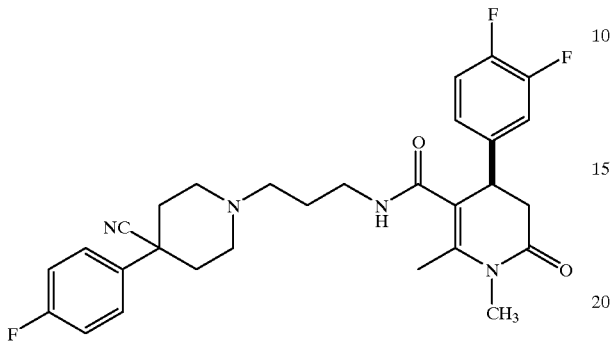

The title compound was prepared from 3-[4-(4-fluorophenyl)-4-cyano-piperidin-1-yl]propylamine (see Example 4) and 4-(R,S)-(3,4-difluorophenyl)-1,6-dimethyl-3,4-dihydro-2-pyridinone-5-carboxylic acid in accordance with General Procedure B. $[\alpha]_D=+5.9°$ (c=0.15, MeOH).

The (S) enantiomer was also resolved from the racemate in the same procedure. $[\alpha]_D=-4.1°$ (c=0.17, MeOH).

EXAMPLE 24

4-(R)-(3,4-Difluorophenyl)-6-methyl-3,4-dihydro-2-pyridinone-5-carboxylic acid{3-[4-(2-cyano-4-fluorophenyl)-4-cyano-piperidine-1-yl]-propyl}amide

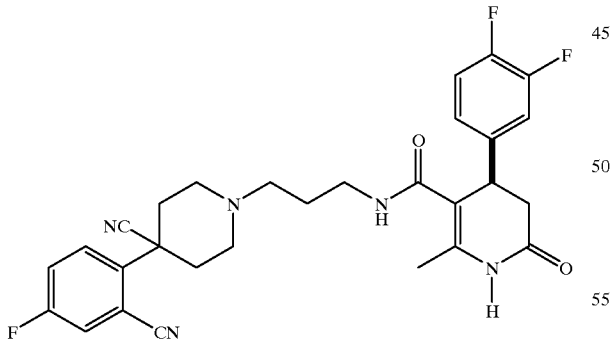

The title compound was prepared from 3-[4-(2-cyano-4-fluorophenyl)-4-cyano-piperidin-1-yl]propylamine (see Example 5) and (−)-4-(R)-(3,4-difluorophenyl)-6-methyl-3,4-dihydro-2-pyridinone-5-carboxylic acid in accordance with General Procedure A.

MS: M+H=536.23.

EXAMPLE 25

4-(R)-(3,4-Difluorophenyl)-1,6-dimethyl-3,4-dihydro-2-pyridinone-5-carboxylic acid{3-[4-(2-cyano-4-fluorophenyl)-4-cyano-piperidine-1-yl]-propyl}amide

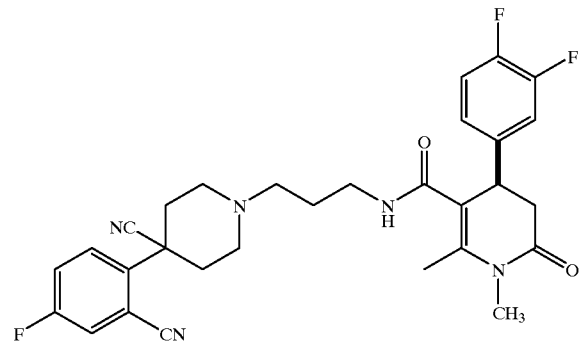

The title compound was prepared from 3-[4-(2-cyano-4-fluorophenyl)-4-cyano-piperidin-1-yl]propylamine (see Example 5) and (+)-4-(R)-(3,4-difluorophenyl)-1,6-dimethyl-3,4-dihydro-2-pyridinone-5-carboxylic acid in accordance with General Procedure A.

MS: M+H=550.24.

EXAMPLE 26

4-(R)-(3,4-Difluorophenyl)-6-methyl-3,4-dihydro-2-pyridinone-5-carboxylic acid{3-[4-(2,4-difluorophenyl)-4-cyano-piperidine-1-yl]-propyl}amide

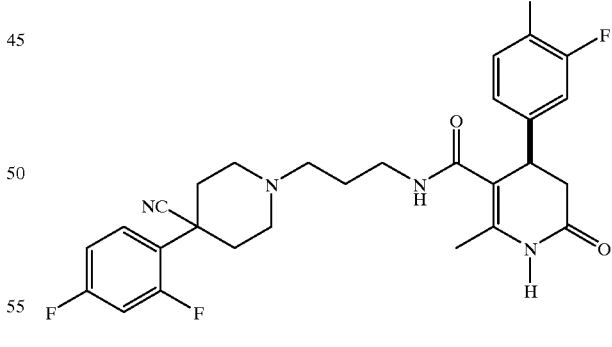

The title compound was prepared from 3-[4-(2,4-difluorophenyl)-4-cyano-piperidin-1-yl]propylamine (see Example 6) and 4-(R,S)-(3,4-difluorophenyl)-6-methyl-3,4-dihydro-2-pyridinone-5-carboxylic acid in accordance with General Procedure B. $[\alpha]_D=-56.7°$ (c=0.18, MeOH).

The (S) enantiomer was also resolved from the racemate in the same procedure. $[\alpha]_D=+54°$ (c=0.17, MeOH).

EXAMPLE 27

4-(R)-(3,4-Difluorophenyl)-1,6-dimethyl-3,4-dihydro-2-pyridinone-5-carboxylic acid{3-[4-(2,4-difluorophenyl)-4-cyano-piperidine-1-yl]-propyl}amide

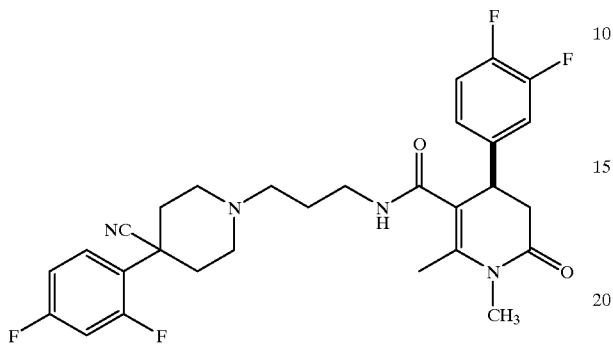

The title compound was prepared from 3-[4-(2,4-difluorophenyl)-4-cyano-piperidin-1-yl]propylamine (see Example 6) and 4-(R,S)-(3,4-difluorophenyl)-1,6-dimethyl-3,4-dihydro-2-pyridinone-5-carboxylic acid in accordance with General Procedure B. $[\alpha]_D=+5°$ (c=0.24, MeOH).

The (S) enantiomer was also resolved from the racemate in the same procedure. $[\alpha]_D=-6°$ (c=0.18, MeOH).

EXAMPLE 28

4-(R)-(3,4-Difluorophenyl)-6-methyl-3,4-dihydro-2-pyridinone-5-carboxylic acid{3-[4-(2-cyanophenyl)-piperidine-1-yl]-propyl}amide

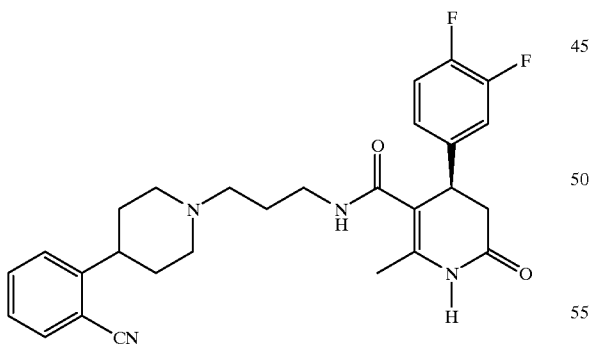

The title compound was prepared from 3-[4-(2-cyanophenyl)-piperidin-1-yl]propylamine (see Example 7) and (−)-4-(R)-(3,4-difluorophenyl)- 6-methyl-3,4-dihydro-2-pyridinone-5-carboxylic acid in accordance with General Procedure A.

MS: M+H=493.24.

EXAMPLE 29

4-(R)-(3,4-Difluorophenyl)-1,6-dimethyl-3,4-dihydro-2-pyridinone-5-carboxylic acid{3-[4-(2-cyanophenyl)-piperidine-1-yl]-propyl}amide

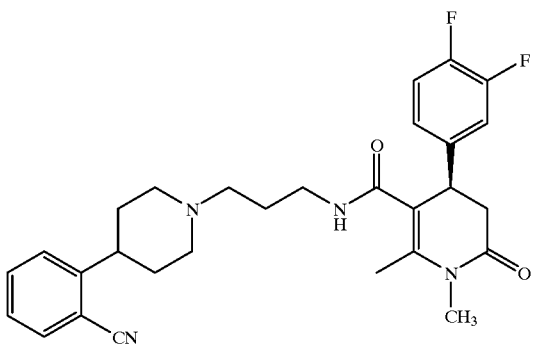

The title compound was prepared from 3-[4-(2-cyanophenyl)-piperidin-1-yl]propylamine (see Example 7) and (+)-4-(R)-(3,4-difluorophenyl)-1,6-dimethyl-3,4-dihydro-2-pyridinone-5-carboxylic acid in accordance with General Procedure A.

MS: M+H=507.26.

EXAMPLE 30

4-(R)-(3,4-Difluorophenyl)-6-methyl-3,4-dihydro-2-pyridinone-5-carboxylic acid{3-[4-(2-cyanophenyl)-4-cyano-piperidine-1-yl]-propyl}amide

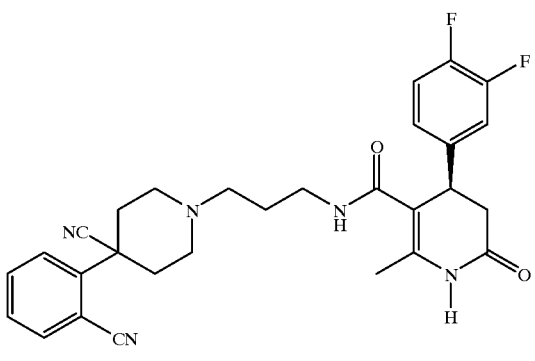

The title compound was prepared from 3-[4-(2-cyanophenyl)-4-cyano-piperidin-1-yl]propylamine (see Example 8) and (−)-4-(R)-(3,4-difluorophenyl)-6-methyl-3,4-dihydro-2-pyridinone-5-carboxylic acid in accordance with General Procedure A.

MS: M+H=518.24.

EXAMPLE 31

4-(R)-(3,4-Difluorophenyl)-1,6-dimethyl-3,4-dihydro-2-pyridinone-5-carboxylic acid{3-[4-(2-cyanophenyl)-4-cyano-piperidine-1-yl]-propyl}amide

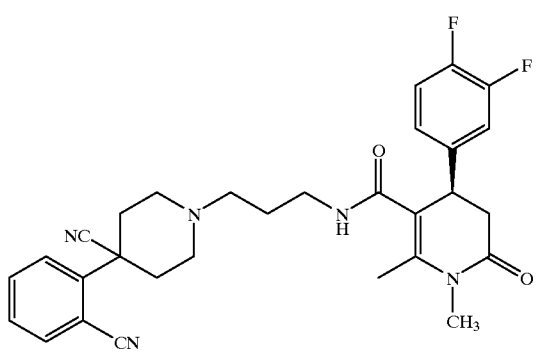

The title compound was prepared from 3-[4-(2-cyanophenyl)-4-cyano-piperidin-1-yl]propylamine (see Example 8) and (+)-4-(R)-(3,4-difluorophenyl)-1,6-dimethyl-3,4-dihydro-2-pyridinone-5-carboxylic acid in accordance with General Procedure A.

MS: M+H=532.26.

EXAMPLE 32

4-(R)-(3,4-Difluorophenyl)-6-methyl-3,4-dihydro-2-pyridinone-5-carboxylic acid{2-[4-(2-cyanophenyl)-cyclohexylamine-N-yl]-ethyl}amide

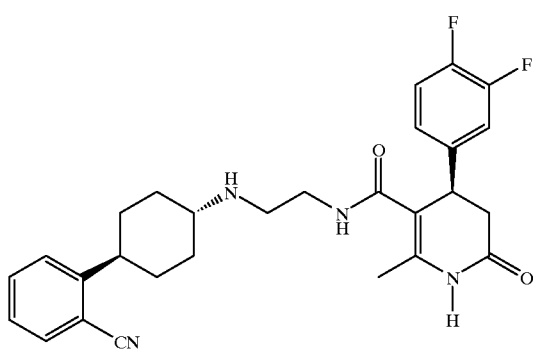

The title compound was prepared from trans 2-[4-(2-Amino-ethylamino)-cyclohexyl]-benzonitrile (see Example 9) and 4-(R,S)-(3,4-difluorophenyl)-6-methyl-3,4-dihydro-2-pyridinone-5-carboxylic acid in accordance with General Procedure B. $[\alpha]_D$=19.4° (c=0.11, MeOH).

The (S) enantiomer was also resolved from the racemate in the same procedure. $[\alpha]_D$=+14.2° (c=0.09, MeOH).

EXAMPLE 33

4-(R)-(3,4-Difluorophenyl)-1,6-dimethyl-3,4-dihydro-2-pyridinone-5-carboxylic acid{2-[4-(2-cyanophenyl)-cyclohexylamine-N-yl]-ethyl}amide

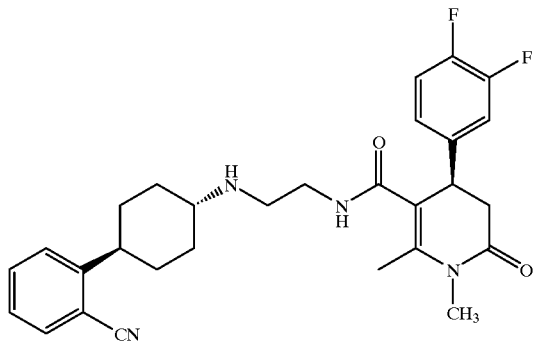

The title compound was prepared trans 2-[4-(2-Amino-ethylamino)-cyclohexyl]-benzonitrile (see Example 9) and (+)-4-(R)-(3,4-difluorophenyl)-1,6-dimethyl-3,4-dihydro-2-pyridinone-5-carboxylic acid in accordance with General Procedure A.

MS: M+H=507.26.

EXAMPLE 34

As a specific embodiment of an oral composition, 100 mg of the compound of Example 20 is formulated with sufficient finely divided lactose to provide a total amount of 580 to 590 mg to fill a size O hard gel capsule.

EXAMPLE 35

Screening Assay: Alpha 1a Adrenergic Receptor Binding

Membranes prepared from the stably transfected human alpha 1a cell line (ATCC CRL 11140) were used to identify compounds that bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from the alpha 1a cell line and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

EXAMPLE 36

Selective Binding Assays

Membranes prepared from stably transfected human alpha 1d and alpha 1b cell lines (ATCC CRL 11138 and CRL 11139, respectively) were used to identify compounds that selectively bind to the human alpha 1a adrenergic receptor. These competition binding reactions (total volume=200 µl) contained 50 mM Tris-HCl pH. 7.4, 5 mM EDTA, 150 mM NaCl, 100 pM [$^{125}$I]-HEAT, membranes prepared from cell lines transfected with the respective alpha 1 subtype expression plasmid and increasing amounts of unlabeled ligand. Reactions were incubated at room temperature for one hour with shaking. Reactions were filtered onto Whatman GF/C glass fiber filters with a Inotec 96 well cell harvester. Filters were washed three times with ice cold buffer and bound radioactivity was determined (Ki).

All of the compounds of the present invention prepared in the foregoing Examples were found to have alpha 1a Ki values of less than 50 nM as determined via the screening assay described in Example 35, except for Example 17 (257 nM). All of the compounds were further found to be at least about 10-fold more selective in binding to alpha 1a receptors versus binding to the alpha 1b and alpha 1d receptors, as determined via the selective binding assay described in the preceding paragraph, except for Example 17 (1a about 8-fold more selective than 1b). All of the compounds except for those of Examples 17, 32 and 33 were at least about 40-fold more selective in binding to alpha 1a receptors versus alpha 1b and 1d receptors.

EXAMPLE 37

Exemplary Counterscreens
1. Assay Title: Dopamine D2, D3, D4 in vitro screen
   Objective of the Assay:
   The objective of this assay is to eliminate agents which specifically affect binding of [3H] spiperone to cells expressing human dopamine receptors D2, D3 or D4.
   Method:
   Modified from VanTol et al (1991); Nature (Vol 350) Pg 610–613.
   Frozen pellets containing specific dopamine receptor subtypes stably expressed in clonal cell lines are lysed in 2 ml lysing buffer (10 mM Tris-HCl/5 mM Mg, pH 7.4). Pellets obtained after centrifuging these membranes (15' at 24,450 rpm) are resuspended in 50 mM Tris-HCl pH 7.4 containing EDTA, MgCl[2], KCl, NaCl, CaCl[2] and ascorbate to give a 1 Mg/mL suspension. The assay is initiated by adding 50–75 $\mu$g membranes in a total volume of 500 $\mu$l containing 0.2 nM [3H]-spiperone. Non-specific binding is defined using 10 $\mu$M apomorphine. The assay is terminated after a 2 hour incubation at room temperature by rapid filtration over GF/B filters presoaked in 0.3% PEI, using 50 mM Tris-HCl pH 7.4.
2. Assay Title: Serotonin 5HT1a
   Objective of the Assay
   The objective of this assay is to eliminate agents which specifically affect binding to cloned human 5HT1a receptor
   Method:
   Modified from Schelegel and Peroutka *Biochemical Pharmacology* 35: 1943–1949 (1986).
   Mammalian cells expressing cloned human 5HT1a receptors are lysed in ice-cold 5 mM Tris-HCl, 2 mM EDTA (pH 7.4) and homogenized with a polytron homogenizer. The homogenate is centrifuged at 1000×g for 30', and then the supernatant is centrifuged again at 38,000×g for 30'. The binding assay contains 0.25 riM [3H]8-OH-DPAT (8-hydroxy-2-dipropylamino-1,2,3,4-tetrahydronaphthalene) in 50 mM Tris-HCl, 4 mM CaCl2 and 1 mg/ml ascorbate. Non-specific binding is defined using 10 $\mu$M propranolol. The assay is terminated after a 1 hour incubation at room temperature by rapid filtration over GF/Cfilters

EXAMPLE 38

Exemplary Functional Assays

In order to confirm the specificity of compounds for the human alpha 1a adrenergic receptor and to define the biological activity of the compounds, the following functional tests may be performed:

1. In vitro Rat, Dog and Human Prostate and Dog Urethra
   Taconic Farms Sprague-Dawley male rats, weighing 250–400 grams are sacrificed by cervical dislocation under anesthesia (methohexital; 50 mg/kg, i.p.). An incision is made into the lower abdomen to remove the ventral lobes of the prostate. Each prostate removed from a mongrel dog is cut into 6–8 pieces longitudinally along the urethra opening and stored in ice-cold oxygenated Krebs solution overnight before use if necessary. Dog urethra proximal to prostate is cut into approximately 5 mm rings, the rings are then cut open for contractile measurement of circular muscles. Human prostate chips from transurethral surgery of benign prostate hyperplasia are also stored overnight in ice-cold Krebs solution if needed.
   The tissue is placed in a Petri dish containing oxygenated Krebs solution [NaCl, 118 mM; KCl, 4.7 mM; CaCl$_2$, 2.5 mM; KH$_2$PO$_4$, 1.2 mM; MgSO$_4$, 1.2 mM; NaHCO$_3$, 2.0 mM; dextrose, 11 mM] warmed to 37° C. Excess lipid material and connective tissue are carefully removed. Tissue segments are attached to glass tissue holders with 4-0 surgical silk and placed in a 5 ml jacketed tissue bath containing Krebs buffer at 37° C., bubbled with 5% CO$_2$/ 95% O$_2$. The tissues are connected to a Statham-Gould force transducer; 1 gram (rat, human) or 1.5 gram (dog) of tension is applied and the tissues are allowed to equilibrate for one hour. Contractions are recorded on a Hewlett-Packard 7700 series strip chart recorder.
   After a single priming dose of 3 $\mu$M (for rat), 10 $\mu$M (for dog) and 20 $\mu$M (for human) of phenylephrine, a cumulative concentration response curve to an agonist is generated; the tissues are washed every 10 minutes for one hour. Vehicle or antagonist is added to the bath and allowed to incubate for one hour, then another cumulative concentration response curve to the agonist is generated.
   EC$_{50}$ values are calculated for each group using GraphPad Inplot software. pA$_2$ (–log K$_b$) values were obtained from Schild plot when three or more concentrations were tested. When less than three concentrations of antagonist are tested, K$_b$ values are calculated according to the following formula $K_b=[B]$, where x is the ratio of EC$_{50}$ of agonist in the presence and absence of antagonist and [B] is the antagonist concentration.
2. Measurement of Intra-Urethral Pressure in Anesthetized Dogs
   PURPOSE: Benign prostatic hyperplasia causes a decreased urine flow rate that may be produced by both passive physical obstruction of the prostatic urethra from increased prostate mass as well as active obstruction due to prostatic contraction. Alpha adrenergic receptor antagonists such as prazosin and terazosin prevent active prostatic contraction, thus improve urine flow rate and provide symptomatic relief in man. However, these are non-selective alpha 1 receptor antagonists which also have pronounced vascular effects. Because we have identified the alpha 1a receptor subtype as the predominant subtype in the human prostate, it is now possible to specifically target this receptor to inhibit prostatic contraction without concomitant changes in the vasculature. The following model is used to measure adrenergically mediated changes in intra-urethral pressure and arterial pressure in anesthetized dogs in order to evaluate the efficacy and potency of selective alpha adrenergic receptor antagonists. The goals are to: 1) identify the alpha 1 receptor subtypes responsible for prostatic/urethral contraction and vascular responses, and 2) use this model to evaluate novel selective alpha adrenergic antagonists. Novel and standard alpha adrenergic antagonists may be evaluated in this manner.

METHODS: Male mongrel dogs (7–12 kg) are used in this study. The dogs are anesthetized with pentobarbital sodium (35 mg/kg, i.v. plus 4 mg/kg/hr iv infusion). An endotracheal tube is inserted and the animal ventilated with room air using a Harvard instruments positive displacement large animal ventilator. Catheters (PE 240 or 260) are placed in the aorta via the femoral artery and vena cava via the femoral veins (2 catheters, one in each vein) for the measurement of arterial pressure and the administration of drugs, respectively. A supra-pubic incision ~½ inch lateral to the penis is made to expose the urethers, bladder and urethra. The urethers are ligated and cannulated so that urine flows freely into beakers. The dome of the bladder is retracted to facilitate dissection of the proximal and distal urethra. Umbilical tape is passed beneath the urethra at the bladder neck and another piece of umbilical tape is placed under the distal urethra approximately 1–2 cm distal to the prostate. The bladder is incised and a Millar micro-tip pressure transducer is advanced into the urethra. The bladder incision is sutured with 2-0 or 3-0 silk (purse-string suture) to hold the transducer. The tip of the transducer is placed in the prostatic urethra and the position of the Millar catheter is verified by gently squeezing the prostate and noting the large change in urethral pressure.

Phenylephrine, an alpha 1 adrenergic agonist, is administered (0.1–100 ug/kg, iv; 0.05 ml/kg volume) in order to construct dose response curves for changes in intra-urethral and arterial pressure. Following administration of increasing doses of an alpha adrenergic antagonist (or vehicle), the effects of phenylephrine on arterial pressure and intra-urethral pressure are re-evaluated. Four or five phenylephrine dose-response curves are generated in each animal (one control, three or four doses of antagonist or vehicle). The relative antagonist potency on phenylephrine induced changes in arterial and intra-urethral pressure are determined by Schild analysis. The family of averaged curves are fit simultaneously (using ALLFIT software package) with a four paramenter logistic equation constraining the slope, minimum response, and maximum response to be constant among curves. The dose ratios for the antagonist doses (rightward shift in the dose-response curves from control) are calculated as the ratio of the $ED_{50}$'s for the respective curves. These dose-ratios are then used to construct a Schild plot and the Kb (expressed as ug/kg, iv) determined. The Kb (dose of antagonist causing a 2-fold rightward shift of the phenylephrine dose-response curve) is used to compare the relative potency of the antagonists on inhibiting phenylephrine responses for intra-urethral and arterial pressure. The relative selectivity is calculated as the ratio of arterial pressure and intra-urethral pressure Kb's. Effects of the alpha 1 antagonists on baseline arterial pressure are also monitored. Comparison of the relative antagonist potency on changes in arterial pressure and intra-urethral pressure provide insight as to whether the alpha receptor subtype responsible for increasing intra-urethral pressure is also present in the systemic vasculature. According to this method, one is able to confirm the selectivity of alpha 1a adrenergic receptor antagonists that prevent the increase in intra-urethral pressure to phenylephrine without any activity at the vasculature.

While the foregoing specification teaches the principles of the present invention, with examples provided for the purpose of illustration, the practice of the invention encompasses all of the usual variations, adaptations and/or modifications that come within the scope of the following claims.

What is claimed is:
1. A compound of formula

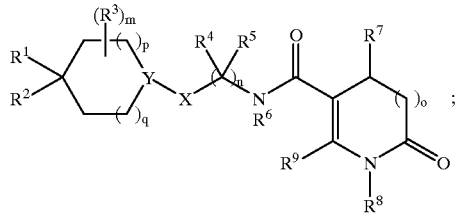

wherein
Y is CH;
X is $NR^6$;
$R^1$ is phenyl, mono- or poly-substituted phenyl, naphthyl, mono- or poly-substituted naphthyl, heterocyclic, or mono- or poly-substituted heterocyclic; wherein the heterocyclic is selected from the group consisting of pyridyl, pyrazinyl, thienyl, thiazolyl, furanyl and quinazolinyl; each of the substituents on the substituted phenyl or substituted naphthyl is independently selected from halo, nitro, cyano, hydroxy, $C_1$–$C_6$ alkyl, $C_3$–$C_8$ cycloalkyl, $C_1$–$C_6$ alkoxy, halogenated $C_1$–$C_6$ alkyl, halogenated $C_3$–$C_8$ cycloalkyl, halogenated $C_1$–$C_6$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substituents on the substituted heterocyclic is independently selected from halo, cyano, nitro, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $C_3$–$C_8$ cycloalkyl, and halogenated $C_3$–$C_8$ cycloalkyl;
$R^2$ is hydrogen, cyano, hydroxy, $C_1$–$C_6$ alkoxy, $CO_2R^c$, $C(=O)N(R^c)_2$, tetrazole, isooxadiazole, phenyl, mono- or poly-substituted phenyl, naphthyl, mono- or poly-substituted naphthyl, heterocyclic, or mono- or poly-substituted heterocyclic; wherein the heterocyclic is selected from the group consisting of pyridyl, thienyl and furanyl; each of the substituents on the substituted phenyl or substituted naphthyl is independently selected from halo, cyano, nitro, hydroxy, $C_1$–$C_6$ alkoxy, halogenated $C_1$–$C_6$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, $(CH_2)_{0-4}SO_2R^c$, $C_1$–$C_6$ alkyl, halogenated $C_1$–$C_6$ alkyl, $C_3$–$C_8$ cycloalkyl, and halogenated $C_3$–$C_8$ cycloalkyl; and each of the substituents on the substituted heterocyclic is independently selected from halo, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, phenyl, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $C_3$–$C_8$ cycloalkyl, and halogenated $C_3$–$C_8$ cycloalkyl;
each $R^3$ is a substituent connected to a ring atom other than $CR^1R^2$ or Y and is independently $C_1$–$C_4$ alkyl;
$R^4$ and $R^5$ are each independently selected from hydrogen, $C_1$–$C_6$ alkyl, and $C_3$–$C_8$ cycloalkyl;
$R^6$ is hydrogen or $C_1$–$C_4$ alkyl;
$R^7$ is phenyl, or mono- or poly-substituted phenyl; wherein each of the substituents on the substituted phenyl is independently selected from halo, nitro, cyano, hydroxy, $C_1$–$C_6$ alkyl, $C_3$–$C_8$ cycloalkyl, $C_1$–$C_6$ alkoxy, halogenated $C_1$–$C_6$ alkyl, halogenated $C_3$–$C_8$ cycloalkyl, halogenated $C_1$–$C_6$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$;

$R^8$ is hydrogen, $C_1$–$C_6$ alkyl, $(CH_2)_{0-4}CO_2R^c$, or $(CH_2)_{0-4}C(=O)R^c$;

$R^9$ is hydrogen, halo, cyano, $C_1$–$C_6$ alkyl, $C_3$–$C_8$ cycloalkyl, $C_1$–$C_6$ alkoxy, halogenated $C_1$–$C_6$ alkyl, halogenated $C_3$–$C_8$ cycloalkyl, halogenated $C_1$–$C_6$ alkoxy, $(CH_2)_{1-4}OR^b$, $CO_2R^c$, $C(=O)R^c$, or $C(=O)N(R^c)_2$;

$R^a$ is hydrogen, $C_1$–$C_6$ alkyl, or halogenated $C_1$–$C_6$ alkyl;

$R^b$ is hydrogen, $C_1$–$C_6$ alkyl, or halogenated $C_1$–$C_6$ alkyl;

$R^c$ and $R^d$ are each independently selected from hydrogen, $C_1$–$C_6$ alkyl, $C_3$–$C_8$ cycloalkyl and $(CH_2)_{1-4}CF_3$;

m is an integer of from 0 to 2;

n is an integer of from 2 to 4;

o is zero; and p and q are each integers of from 0 to 2, wherein the sum of p+q is less than or equal to 3;

or a pharmaceutically acceptable salt thereof.

2. The compound according to claim 1, wherein $R^1$ is phenyl, mono- or di-substituted phenyl, naphthyl, mono- or di-substituted naphthyl, heterocyclic, or mono- or di-substituted heterocyclic;

$R^2$ is hydrogen, cyano, hydroxy, $C_1$–$C_6$ alkoxy, $CO_2R^c$, $C(=O)N(R^c)_2$, tetrazole, isooxadiazole, phenyl, mono- or di-substituted phenyl, naphthyl, mono- or di-substituted naphthyl, heterocyclic, or mono- or di-substituted heterocyclic; and $R^7$ is selected from phenyl, or mono- or di-substituted phenyl;

or a pharmaceutically acceptable salt thereof.

3. The compound according to claim 1, wherein $R^1$ is phenyl, mono- or di-substituted phenyl, pyridyl, or mono- or di-substituted pyridyl; wherein each of the substituents on the substituted phenyl is independently selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substituents on the substituted pyridyl is independently selected from halo, cyano, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1$–$C_4$ alkyl, halogenated $C_1$–$C_4$ alkyl, $C_1$–$C_4$ alkoxy, halogenated $C_1$–$C_4$ alkoxy, and $(CH_2)_{1-4}OR^a$;

$R^2$ is hydrogen, cyano, hydroxy, $C_1$–$C_6$ alkoxy, $CO_2R^c$, $C(=O)N(R^c)_2$, phenyl, mono- or di-substituted phenyl, pyridyl, or mono- or di-substituted pyridyl; wherein each of the substituents on the substituted phenyl is independently selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, and $(CH_2)_{0-4}SO_2R^c$; and each of the substituents on the substituted pyridyl is independently selected from halo, $C_1$–$C_4$ alkyl, halogenated $C_1$–$C_4$ alkyl, $C_1$–$C_4$ alkoxy, halogenated $C_1$–$C_4$ alkoxy, $(CH_2)_{1-4}OR^a$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$;

$R^7$ is phenyl, or mono- or poly-substituted phenyl; wherein each of the substituents on the substituted phenyl is independently selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, and $SO_2R^c$;

$R^a$ is hydrogen, $C_1$–$C_4$ alkyl, or halogenated $C_1$–$C_4$ alkyl;

$R^b$ is hydrogen, $C_1$–$C_4$ alkyl, or halogenated $C_1$–$C_4$ alkyl; and $R^c$ and $R^d$ are each independently selected from hydrogen, $C_1$–$C_4$ alkyl and $(CH_2)_{1-2}CF_3$;

or a pharmaceutically acceptable salt thereof.

4. The compound according to claim 1, wherein $R^1$ is phenyl, or mono- or di-substituted phenyl, pyridyl, or mono- or di-substituted pyridyl; wherein each of the substituents on the substituted phenyl is independently selected from halo, cyano, hydroxy, $C_1$–$C_4$ alkyl, $C_1$–$C_4$ alkoxy, halogenated $C_1$–$C_4$ alkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, and $(CH_2)_{0-4}SO_2R^c$; and each of the substituents on the substituted pyridyl is independently selected from halo, cyano, $N(R^c)_2$, $(CH_2)_{0-4}CO_2R^c$, $(CH_2)_{0-4}C(=O)N(R^c)_2$, $(CH_2)_{0-4}SO_2N(R^c)_2$, $(CH_2)_{0-4}SO_2R^c$, $C_1$–$C_4$ alkyl, halogenated $C_1$–$C_4$ alkyl, $C_1$–$C_4$ alkoxy, halogenated $C_1$–$C_4$ alkoxy, and $(CH_2)_{1-4}OR^a$;

$R^2$ is hydrogen, cyano, hydroxy, $C_1$–$C_6$ alkoxy, $CO_2R^c$, or $C(=O)N(R^c)_2$;

$R^4$ and $R^5$ are either both hydrogen, or one of $R^4$ and $R^5$ is hydrogen and the other is hydrogen, $C_1$–$C_6$ alkyl, or $C_3$–$C_8$ cycloalkyl;

$R^7$ is phenyl, or mono- or di-substituted phenyl; wherein each of the substituents on the substituted phenyl is independently selected from halo, cyano, hydroxy, $C_1$–$C_4$ alkyl, $C_1$–$C_4$ alkoxy, $(CH_2)_{1-4}OR^b$, $(CH_2)_{0-4}CF_3$, $OCF_3$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, and $SO_2R^c$; and $R^b$ is $C_1$–$C_4$ alkyl or $CF_3$;

or a pharmaceutically acceptable salt thereof.

5. The compound according to claim 1, wherein the compound is of formula

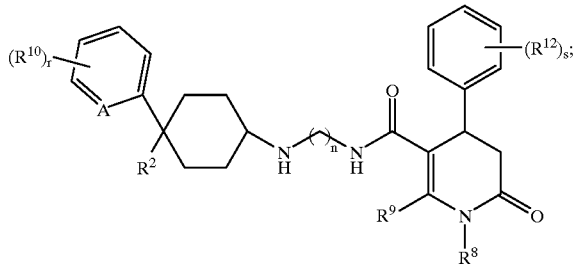

wherein

A is $CR^{10}$ or N;

$R^2$ is hydrogen, cyano, hydroxy, $C_1$–$C_6$ alkoxy, $CO_2R^c$, $C(=O)N(R^c)_2$, phenyl, or mono- or poly-substituted phenyl; wherein each of the substituents on the substituted phenyl is independently selected from halo, cyano, nitro, hydroxy, $C_1$–$C_6$ alkyl, halogenated $C_1$–$C_6$ alkyl, $C_1$–$C_6$ alkoxy, halogenated $C_1$–$C_6$ alkoxy, $(CH_2)_{1-4}OR^a$, $(CH_2)_{0-4}CO_2R^c$, $(CH_2)_{0-4}C(=O)N(R^c)_2$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}SO_2N(R^c)_2$, and $(CH_2)_{0-4}SO_2R^c$;

$R^8$ is hydrogen, $C_1$–$C_4$ alkyl, $(CH_2)_{0-4}CO_2R^c$, or $(CH_2)_{0-4}C(=O)R^c$;

$R^9$ is hydrogen, halo, cyano, $C_1$–$C_6$ alkyl, $C_3$–$C_6$ cycloalkyl, $C_1$–$C_6$ alkoxy, halogenated $C_1$–$C_6$ alkyl, halogenated $C_1$–$C_6$ alkoxy, $(CH_2)_{1-4}OR^b$, $CO_2R^c$, $C(=O)R^c$, or $C(=O)N(R^c)_2$;

each $R^{10}$ is independently hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

each $R^{12}$ is independently hydrogen, halo, nitro, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $NR^cSO_2N(R^d)_2$, $(CH_2)_{0-4}CO_2R^c$, $(CH_2)_{0-4}C(=O)N(R^c)_2$, $(CH_2)_{0-4}SO_2N(R^c)_2$, or $(CH_2)_{0-4}SO_2R^c$;

n is an integer of from 2 to 4; and r and s are independently integers of from 0 to 2;

or a pharmaceutically acceptable salt thereof.

6. The compound according to claim 5, wherein the compound is a (+) enantiomer; or a pharmaceutically acceptable salt thereof.

7. The compound according to claim 5, wherein the compound is a (−) enantiomer; or a pharmaceutically acceptable salt thereof.

8. The compound according to claim 5, wherein $R^2$ is hydrogen, cyano, hydroxy, $C_1$–$C_4$ alkoxy, $CO_2R^c$, $C(=O)N(R^c)_2$, phenyl, or mono- or poly-substituted phenyl; wherein each of the substituents on the substituted phenyl is independently selected from halo, cyano, hydroxy, $C_1$–$C_4$ alkyl, halogenated $C_1$–$C_4$ alkyl, $C_1$–$C_4$ alkoxy, halogenated $C_1C_4$ alkoxy, $CO_2R^c$, $C(=O)N(R^c)_2$, $N(R^c)_2$, $NR^cC(=O)R^d$, $NR^cC(=O)N(R^d)_2$, $NR^cSO_2R^d$, $SO_2N(R^c)_2$, and $SO_2R^c$;

$R^8$ is hydrogen, $C_1$–$C_4$ alkyl, $CO_2R^c$, or $C(=O)R^c$;

$R^9$ is hydrogen, halo, cyano, $C_1$–$C_4$ alkyl, $C_3$–$C_6$ cycloalkyl, $C_1$–$C_4$ alkoxy, halogenated $C_1$–$C_4$ alkyl, halogenated $C_1$–$C_4$ alkoxy, $(CH_2)_{1-4}OR^b$, $CO_2R^c$, $C(=O)R^c$, or $C(=O)N(R^c)_2$;

each $R^{10}$ is independently hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^a$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

each $R^{12}$ is independently hydrogen, halo, cyano, hydroxy, $C_1$–$C_4$ alkyl, $C_3$–$C_6$ cycloalkyl, $C_1$–$C_4$ alkoxy, halogenated $C_1$–$C_4$ alkyl, halogenated $C_3$–$C_6$ cycloalkyl, halogenated $C_1$–$C_4$ alkoxy, $(CH_2)_{1-4}OR^b$, $N(R^c)_2$, $NR^cC(=O)R^d$, $NR^cC(=O)N(R^d)_2$, $NR^cSO_2R^d$, $CO_2R^c$, $C(=O)N(R^c)_2$, $SO_2N(R^c)_2$, or $SO_2R^c$;

$R^a$ is hydrogen, $C_1$–$C_4$ alkyl, or halogenated $C_1$–$C_4$ alkyl;

$R^b$ is hydrogen, $C_1$–$C_4$ alkyl, or halogenated $C_1$–$C_4$ alkyl; and $R^c$ and $R^d$ are each independently selected from hydrogen and $C_1$–$C_4$ alkyl;

or a pharmaceutically acceptable salt thereof.

9. The compound according to claim 8, wherein $R^2$ is hydrogen, cyano, hydroxy, $C_1$–$C_4$ alkoxy, $CO_2R^c$, or $C(=O)N(R^c)_2$;

or a pharmaceutically acceptable salt thereof.

10. The compound according to claim 9, wherein the compound is selected from the group consisting of 4-(R)-(3,4-difluorophenyl)-6-methyl-3,4-dihydro-2-pyridinone-5-carboxylic acid{2-[4-(2-cyanophenyl)-cyclohexylamine-N-yl]-ethyl}amide;

4-(S)-(3,4-difluorophenyl)-6-methyl-3,4-dihydro-2-pyridinone-5-carboxylic acid{2-[4-(2-cyanophenyl)-cyclohexylamine-N-yl]-ethyl}amide;

4-(R)-(3,4-difluorophenyl)-1,6-dimethyl-3,4-dihydro-2-pyridinone-5-carboxylic acid{2-[4-(2-cyanophenyl)-cyclohexylamine-N-yl]-ethyl}amide; and pharmaceutically acceptable salts thereof.

11. A pharmaceutical composition comprising the compound according to claim 1 and a pharmaceutically acceptable carrier.

12. A pharmaceutical composition made by combining the compound according to claim 1 and a pharmaceutically acceptable carrier.

13. A process for making a pharmaceutical composition comprising combining the compound according to claim 1 and a pharmaceutically acceptable carrier.

14. The composition according to claim 11 further comprising a testosterone 5-alpha reductase inhibitor.

15. The composition according to claim 14, wherein the testosterone 5-alpha reductase inhibitor is a type 1, a type 2, both a type 1 and a type 2 or a dual type 1 and type 2 testosterone 5-alpha reductase inhibitor.

16. The composition according to claim 15, wherein the testosterone 5-alpha reductase inhibitor is a type 2 testosterone 5-alpha reductase inhibitor.

17. The composition according to claim 16, wherein the testosterone 5-alpha reductase inhibitor is finasteride.

18. A method of treating benign prostatic hyperplasia in a subject in need thereof which comprises administering to the subject a therapeutically effective amount of the compound according to claim 1.

19. The method according to claim 18, wherein the compound does not cause a fall in blood pressure at dosages effective to alleviate benign prostatic hyperplasia.

20. The method according to claim 18, wherein the compound is administered in combination with a testosterone 5-alpha reductase inhibitor.

21. The method according to claim 20, wherein the testosterone 5-alpha reductase inhibitor is finasteride.

22. A method of treating benign prostatic hyperplasia in a subject in need thereof which comprises administering a therapeutically effective amount of the composition according to claim 11.

23. The method according to claim 22, wherein the composition further comprises a therapeutically effective amount of a testosterone 5-alpha reductase inhibitor.

24. A method of relaxing lower urinary tract tissue in a subject in need thereof which comprises administering to the subject a therapeutically effective amount of the compound according to claim 1.

25. The method according to claim 24, wherein the compound is administered in combination with a testosterone 5-alpha reductase inhibitor.

26. The method according to claim 25, wherein the testosterone 5-alpha reductase inhibitor is finasteride.

27. A method of treating a condition which is in need of alpha 1a adrenergic receptor antagonism in a subject comprises administering to said subject an amount of a compound according to claim 1 effective to treat said condition.

28. A method of eliciting an alpha 1a adrenergic receptor antagonizing effect in a mammal in need thereof, comprising administering to the mammal a therapeutically effective amount of the compound according to claim 1.

* * * * *

UNITED STATES PATENT AND TRADEMARK OFFICE
CERTIFICATE OF CORRECTION

PATENT NO. : 6,235,759 B1
DATED : May 22, 2001
INVENTOR(S) : J.C. Barrow, P.G. Nantermet, H.G. Selnick It is certified that error appears in the above-identified patent and that said Letters Patent is hereby corrected as shown below:

Title page,
Item [75], please delete

"James C. Barrow, Harleysville;
Philippe G. Nanterment, Lansdale;
Harold G. Selnick, Ambler, all of PA
(US)"

and in its place insert

-- James C. Barrow, Harleysville;
Philippe G. Nantermet, Lansdale;
Harold G. Selnick, Ambler, all of PA
(US) --.

Signed and Sealed this

Fourth Day of December, 2001

*Attest:*

*Attesting Officer*

NICHOLAS P. GODICI
*Acting Director of the United States Patent and Trademark Office*